(12) United States Patent
Pfeifer et al.

(10) Patent No.: US 10,071,027 B2
(45) Date of Patent: Sep. 11, 2018

(54) DENTAL COMPOSITES

(71) Applicant: OREGON HEALTH & SCIENCE UNIVERSITY, Portland, OR (US)

(72) Inventors: Carmem S. Pfeifer, Portland, OR (US); Jack L. Ferracane, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/126,751

(22) PCT Filed: Mar. 17, 2015

(86) PCT No.: PCT/US2015/021016
§ 371 (c)(1),
(2) Date: Sep. 16, 2016

(87) PCT Pub. No.: WO2015/142886
PCT Pub. Date: Sep. 24, 2015

(65) Prior Publication Data
US 2017/0087062 A1 Mar. 30, 2017

Related U.S. Application Data

(60) Provisional application No. 62/020,491, filed on Jul. 3, 2014, provisional application No. 62/012,647, filed on Jun. 16, 2014, provisional application No. 61/954,319, filed on Mar. 17, 2014.

(51) Int. Cl.
| A61K 6/083 | (2006.01) |
| A61K 6/087 | (2006.01) |
| C08G 18/38 | (2006.01) |
| C08G 18/08 | (2006.01) |
| A61K 6/02 | (2006.01) |
| C07C 271/20 | (2006.01) |
| A61K 6/00 | (2006.01) |

(52) U.S. Cl.
CPC ............ *A61K 6/083* (2013.01); *A61K 6/0023* (2013.01); *C07C 271/20* (2013.01)

(58) Field of Classification Search
USPC ...................................... 523/116; 528/60, 66
See application file for complete search history.

(56) References Cited

U.S. PATENT DOCUMENTS

| 2,994,671 | A | * | 8/1961 | Thompson | C08J 5/06 156/292 |
| 6,653,050 | B2 | | 11/2003 | Fujimaki et al. | |
| 7,767,779 | B2 | | 8/2010 | Jallouli et al. | |
| 2009/0012202 | A1 | * | 1/2009 | Jacobine | C08G 18/44 522/90 |
| 2009/0124762 | A1 | | 5/2009 | Brown et al. | |
| 2010/0307378 | A1 | * | 12/2010 | Trujillo-Lemon | A61K 6/083 106/35 |
| 2011/0144227 | A1 | * | 6/2011 | Bowman | A61L 27/18 522/96 |

OTHER PUBLICATIONS

PCT/US2015/021016 Written Opinion of the International Searching Authority, dated Jun. 8, 2015.
PCT/US2015/021016 International Search Report, dated Jun. 8, 2015.
Boaro et al., Polymerization stress, shrinkage and elastic modulus of current low-shrinkage restorative composites, Dental Materials, 26 (2000) pp. 1144-1150.
Beigi et al., Evaluation of fracture toughness and mechanical properties of ternary thiol-ene-methacrylate systems as resin matrix for dental restorative composites, Dental Materials 29 (2013) pp. 777-787.
Berchtold et al., Coupling Chain Length Dependent and Reaction Diffusion Controlled Termination in the Free Radical Polymerization of Multivinyl (Meth)acrylates, Macromolecules 2002, 35, pp. 7968-7975.
Boulden et al., Thiol-ene-methacrylate composites as dental restorative materials, Dental Materials 27 (2011) pp. 267-272.
Braga et al., Polymerization contraction stress in dual-cure cements and its effect on interfacial integrity of bonded inlays, Journal of Dentistry 30 (2002) pp. 333-340.
Burke et al., Two year clinical evaluation of a low-shrink resin composite material in UK general dental practices, Dental Materials 27 (2011) pp. 622-630.
Carioscia et al., Thiol-ene oligomers as dental restorative materials, Dental Materials (2005) 21, pp. 1137-1143.
Carioscia et al., Thiol-Norbornene Materials: Approaches to Develop High Tg Thiol-Ene Polymers, J Polymer Sci Part A Polymer Chem, 2007, pp. 5686-5696.
Carvalho et al., Durability of bonds and clinical success of adhesive restorations, Dental Materials 28 (2012) pp. 72-86.
Chan et al., The effects of primary amine catalyzed thio-acrylate Michael reaction on the kinetics, mechanical and physical properties of thio-acrylate networks, European Polymer Journal 45 (2009) pp. 2717-2725.
Cramer et al., Properties of methacrylate-thiol-ene formulations as dental restorative materials, Dental Materials 26 (2010) pp. 799-806.
Cramer et al., Investigation of thiol-ene and thiol-ene-methacrylate based resins as dental restorative materials, Dental Materials 26 (2010) pp. 21-28.
Demarco et al., Longevity of posterior composite restorations: Not only a matter of materials, Dental Materials 28 (2012) pp. 87-101.
Esfandiari et al., Efficient Stabilization of Thiol-ene Formulations in Radical Photopolymerization, J Polymer Sci Part A Polymer Chem, 2013, 51, pp. 4261-4266.
Hoyle et al., Thiol-Enes: Chemistry of the Past with Promise for the Future, J Polymer Sci Part A Polymer Chem, 42, 2004 pp. 5301-5338.

(Continued)

*Primary Examiner* — Tae H Yoon

(57) ABSTRACT

Disclosed herein are methacrylate compounds that can be used as components of dental composites. Also disclosed are dental composites comprising the compositions and thiourethane oligomers.

19 Claims, 13 Drawing Sheets

(56) References Cited

OTHER PUBLICATIONS

Li et al., Thiourethane-Based Thiol-Ene High Tg Networks: Preparation, Thermal, Mechanical, and Physical Properties, J Polymer Sci Part A Polymer Chem, 2007, vol. 45, pp. 5103-5111.

Li et al., The Thiol-Isocyanate Click Reaction: Facile and Quantitative Access to ω-End-Functional Poly(N,N-diethylacrylamide) Synthesized by RAFT Radical Polymerization, Macromolecules 2009, 42, pp. 6537-6542.

Li et al., Comparison of Small Molecule and Polymeric Urethanes,Thiourethanes, and Dithiourethanes: Hydrogen Bonding and Thermal, Physical, and Mechanical PropertiesMacromolecules 2009, 42, pp. 1824-1833.

Li et al., Low temperature cure of unsaturated polyester resins with thermoplastic additives II. Structure formation and shrinkage control mechanism, Polymer 41 (2000) pp. 697-710.

Lu et al., Investigations of step-growth thiol-ene polymerizations for novel dental restoratives, Dental Materials (2005) 21, pp. 1129-1136.

Manso et al., Cements and Adhesives for All-Ceramic Restorations, Dental Clin N Amer 55 (2011) pp. 311-332.

Meyer et al., Compomers: between glass-ionomer cements and composites, Biomaterials, 19 (1998) pp. 529-539.

Moraes et al., Control of polymerization shrinkage and stress in nanogel-modified monomer and composite materials, Dental Materials 27 (2011) pp. 509-519.

Park et al., Measuring the residual stress in dental composites using a ring slitting method, Dental Materials (2005) pp. 882-889.

Park et al., Stress relaxation of trithiocarbonate-dimethacrylate-based dental composites, Dental Materials 28 (2012) pp. 888-893.

Peumans et al., Porcelain veneers: a review of the literature, Journal of Dentistry 28 (2000) pp. 163-177.

Pfeifer et al., Factors Affecting Photopolymerization Stress in Dental Composites, J Dent Res 87(11); pp. 1043-1047; 2008.

Pfeifer et al., Delayed gelation through chain-transfer reactions: Mechanism for stress reduction in methacrylate networks, Polymer 52 (2011) pp. 3295-3303.

Rosenstiel et al., Dental luting agents: A review of the current literature, The Journal of Prosthetic Dentistry, vol. 80, No. 3, pp. 280-301, Sep. 1998.

Senyurt et al., Ternary Thiol-Ene/Acrylate Photopolymers: Effect of Acrylate Structure on Mechanical Properties, Macromolecules 2007, 40, pp. 4901-4909.

Shin et al., Segmented Polythiourethane Elastomers through Sequential Thiol-Ene and Thiol-Isocyanate Reactions, Macromolecules 2009, 42, pp. 3294-3301.

Stansbury et al., Determination of double bond conversion in dental resins by near infrared spectroscopy, Dental Materials 17 (2001) pp. 71-79.

Trujillo-Lemon et al., Dimethacrylate Derivatives of Dimer Acid, J Polymer Sci Part A Polymer Chem, 2006, vol. 46, pp. 3921-3929.

Watts et al., Axial shrinkage-stress depends upon both C-factor and composite mass, Dental Materials 24 (2008) pp. 1-8.

Weinmann et al., Siloranes in dental composites, Dental Materials (2005) 21, pp. 68-74.

Yamasaki et al., Polymerization development of "low-shrink" resin composites: Reaction kinetics, polymerization stress and quality of network, Dental Materials 29 (2013) e169-e179.

* cited by examiner

DENTAL COMPOSITES

CROSS-REFERENCE TO RELATED APPLICATION

This U.S. National Stage Application claims priority from PCT/US2015/021016 filed Mar. 17, 2015, which claims the benefit of U.S. Provisional Applications 61/954,319 filed Mar. 17, 2014, 62/012,647 filed Jun. 16, 2014 and 62/020,491 filed Jul. 3, 2014, the entirety of which are incorporated herein by reference.

ACKNOWLEDGEMENT OF GOVERNMENT SUPPORT

The work that resulted in this invention was funded in part by the United States Government under the terms of Grant Number 1R15 DE023211 01A1 and Grant Number 1U01 DE02756 01 awarded by the National Institutes of Health. The United States Government has certain rights to this invention.

FIELD

Generally, the field is dental composites. More specifically, the field is dental composites comprising methacrylamides and thiourethane oligomers.

BACKGROUND

Dental caries is a serious public health issue throughout the U.S., especially more evident in underserved and elderly populations. When preventative measures fail, the best case scenario is for restorations to be long lasting and reliable. Unfortunately, even with the major advances of adhesive dentistry, hundreds of thousands of resin composite restorations have to be replaced each year. The average life-span of this type of restoration is 5-10 years or lower, depending on the caries risk level of the patient (Demarco F F *Dental Materials* 28, 87-101 (2012); incorporated by reference herein). The causes of premature failure are complex; however, contributing factors include polymerization stress (Park H Y et al *Dental Materials* 28, 888-893 (2012)); incorporated by reference herein)—which immediately challenges the bonded interface—and fracture (Demarco 2012 supra). The vast majority of current commercially available resin systems are based on dimethacrylate polymerizations that undergo vitrification at relatively early stages of conversion. Early vitrification increases the potential for stress development at both the bonded interface and in the bulk of the material.

In spite of the many efforts to improve dental resin composite formulations (Stansbury J W et al, *J Dent Res* 71, 1408-1412 (1992); Carioscia J A et al, *Dent Mater* 21, 1137-1143 (2005); Weinmann W et al, *Dent Mater* 21, 68-74 (2005); Trujillo-Lemon M, *J Polymer Sci Part A—Polymer Chem* 44, 3921-3929 (2006); all of which are incorporated by reference herein) replacement of restorations failing from secondary decay and fracture is a common occurrence in daily practice, costing millions of dollars annually. Restoration failure has been attributed to (i) degradation of the tooth-restoration interface and polymerization stress, resulting in gap formation (Carvalho R M et al, *Dental Materials* 28, 72-86 (2012); incorporated by reference herein) and (ii) residual stress concentrating within the bulk of the material (Park J W, *Dental Materials* 21, 882-889 (2005); incorporated by reference herein).

To date, materials developed to reduce shrinkage and stress have proven inefficient at extending the service life of restorations (Burke F J T et al, *Dental Materials* 27, 622-630 (2011); incorporated by reference herein). Furthermore, clinical research has failed to show a correlation between gap formation and secondary decay. This stems from the multi-factorial nature of dental caries, as well as the extremely technique-sensitive placement of composite restorations by practitioners. In addition, stress reductions reported for the few "low-shrink" materials available ranged from 5 to 25% (Boaro L C C, *Dental Materials* 26, 1144-1159 (2010) and Li Y et al, *J Appl Polymer Sci* 124, 436-443 (2012); both of which are incorporated by reference herein). This level of stress reduction may not be sufficient to produce appreciable clinical improvement. Clearly the problem of shrinkage and stress still persists, and millions of restorations are replaced every year due to fracture and marginal failure.

SUMMARY

Currently available dental composites are prone to fracture and degradation at the bonded interface. The disclosed material has at least two-fold greater toughness and 50% less polymerization stress than currently available materials. These properties of the disclosed composite are the result of a higher degree of polymerization due to chain transfer reactions of the thiol to vinyl functional groups (such as methacrylates, acrylates, methacrylamides, and acrylamides); improved mechanical properties due to the introduction of thiourethane bonds; and resistance to hydrolytic degradation resulting from the use of acrylamide and/or methacrylamide monomers.

Disclosed herein are compounds of the formula:

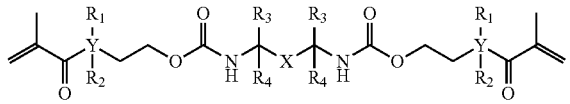

wherein X is aryl or 1-4 carbon alkyl; wherein Y is N or C, wherein $R_1$ is H or alkyl and $R_2$ is no atom when Y is N; wherein $R_1$ is H or alkyl and $R_2$ is H or alkyl when Y is C; and wherein $R_3$ and $R_4$ are H or alkyl; provided that $R_1$ and $R_2$ are not H when X is butyl.

Also disclosed herein are dental composites comprising thiourethane oligomers, dimethacrylates, and filler compositions. The dental composites and cements can be light cured cements or dual cured cements and can further comprise a tertiary amine, an inhibitor, and d-camphorquinone.

Further disclosed are methods of making dental composites, the methods include generating a thiourethane oligomer by contacting an isocyanate compound selected from 1,6-hexanediol-diiosocyante or 1,3-bis(1-isocyanato-1-methylethylbenzene) with a thiol compound selected from pentaerythritol tetra-3-mercaptopropionate or trimethylol-tris-3-mercaptopropionate in the presence of triethanolamine and adding the resulting thiourethane oligomer to the cement. The methods further include adding a dimethacrylate composition to the cement. The dimethacrylate composition can comprise bisphenol A diglycidyl dimethacrylate, urethane dimethacrylate, and tri-ethylene glycol dimethacrylate or any of the disclosed dimethacrylate compositions herein. The methods further include adding tertiary amine, d-camphorquinone and an inhibitor to the cement. The methods still further comprise adding a filler composition to the cement. The thiourethane oligomer comprises at least 10% of the cement.

It is an object of the invention to provide a dental composite with improved mechanical qualities relative to currently available cements including lessened polymerization stress and greater fracture toughness.

DETAILED DESCRIPTION

Figure 1:
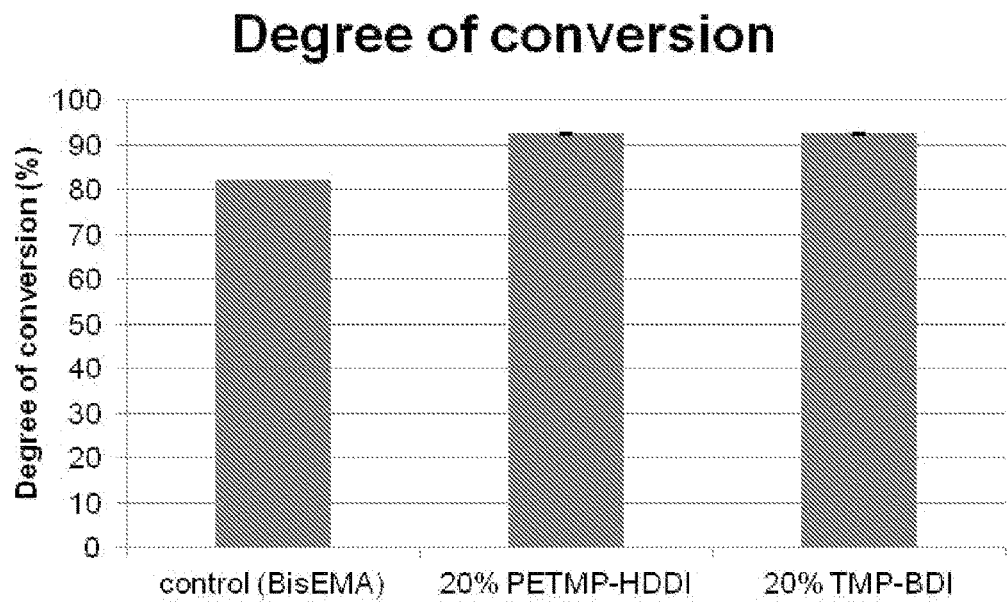
FIG. 1: Degree of conversion measured in near-IR (vinyl peak conversion at 6165 cm$^{-1}$) for resin specimens polymerized with 320-500 nm at 800 mW/cm$^2$. Materials are comprised of a methacrylate matrix (ethoxylated bis-phenol A methacrylate, BisEMA) modified by the addition of 20 wt % oligomers (PETMP-HDDI: aliphatic or TEMP-BDI: aromatic).
Figure 2:
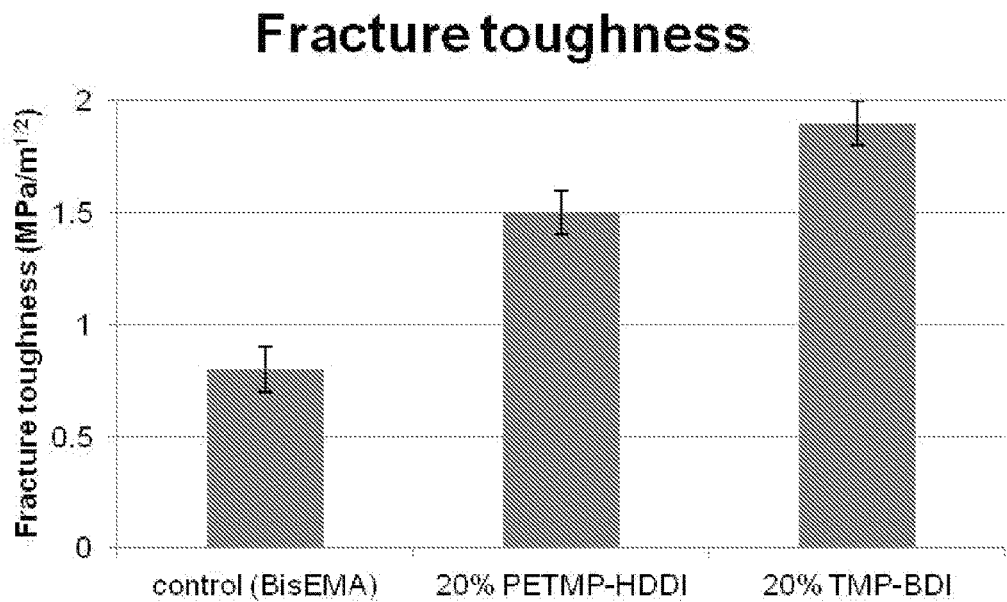
FIG. 2: Fracture toughness measured in 2×5×25 mm notched specimens in three-point bending (ISO 4049). Specimens are polymerized with three overlapping light exposures (320-500 nm at 800 mW/cm$^2$) and tested until failure at 0.5 mm/min. Materials are comprised of a methacrylate matrix (ethoxylated bis-phenol A methacrylate, BisEMA) modified by the addition of 20 wt % oligomers (PETMP-HDDI: aliphatic or TEMP-BDI: aromatic).
Figure 3:
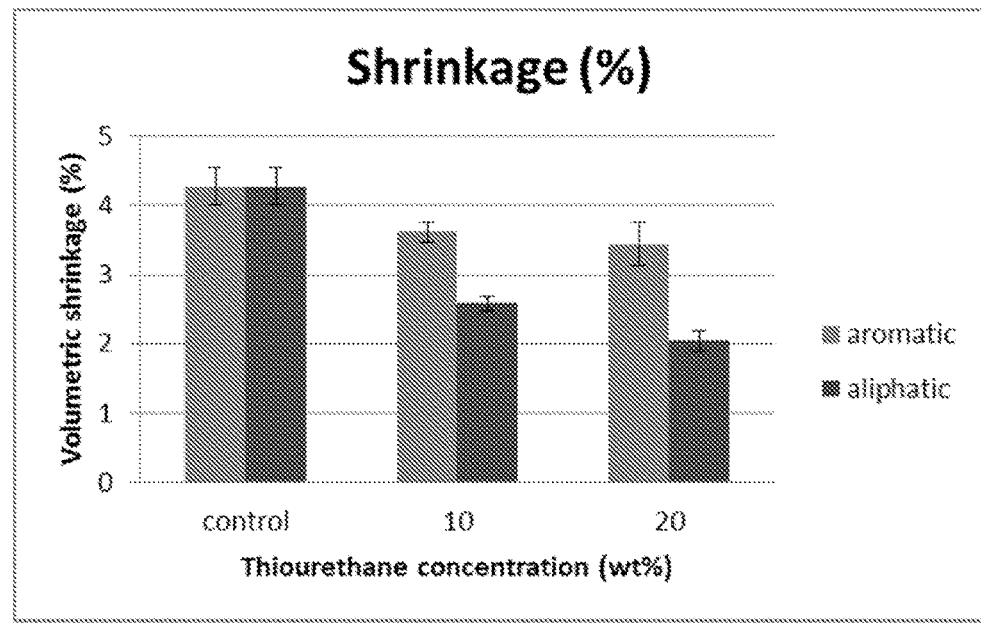
FIG. 3: Polymerization shrinkage measured in a mercury dilatometer (ADA Foundation). Specimens are polymerized through a glass slide at 320-500 nm at 800 mW/cm$^2$ while shrinkage is followed by a linear variable differential transformer (LVDT) coupled to a mercury column. Composite materials are comprised of a methacrylate matrix (ethoxylated bis-phenol A methacrylate, BisEMA, bisphenol A methacrylate, BisGMA and urethane dimethacrylate, UDMA) modified by the addition of 10 or 20 wt % oligomers (PETMP-HDDI: aliphatic or TEMP-BDI: aromatic). The filler used in this composition was comprised of 85 wt % Barium glass and 15 wt % colloidal silica (OX-50), added at 75 wt % of the total mass of the composite.
Figure 4:
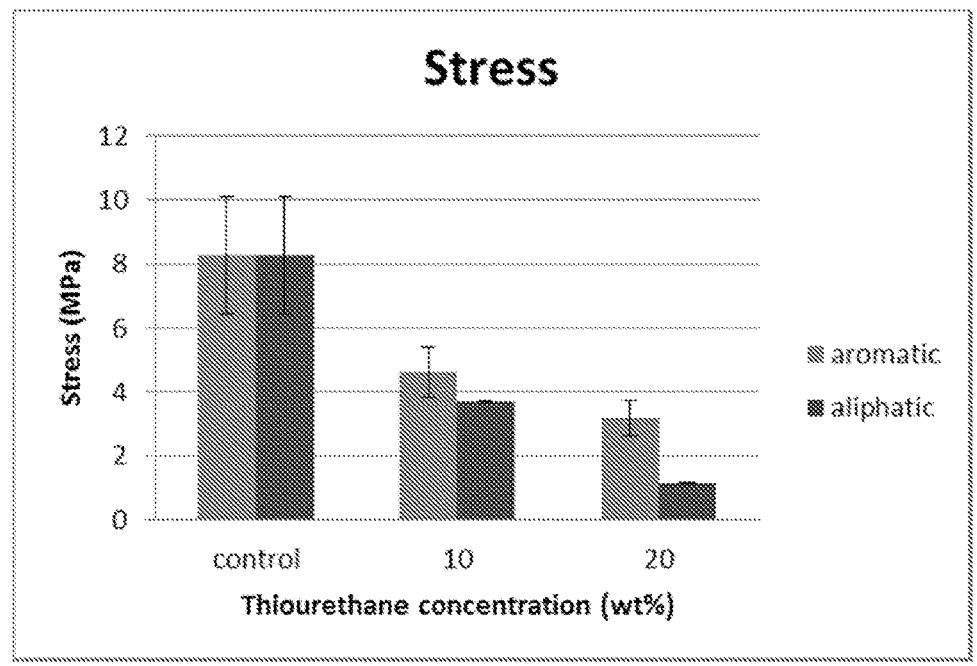
FIG. 4: Polymerization shrinkage stress measured in a cantilever beam device (Bioman, University of Manchester, UK). Specimens are polymerized through a glass slide at 320-500 nm at 800 mW/cm$^2$ while stress is followed by a load cell coupled to the cantilever beam. Composite materials are comprised of a methacrylate matrix (ethoxylated bis-phenol A methacrylate, BisEMA, bisphenol A methacrylate, BisGMA and urethane dimethacrylate, UDMA) modified by the addition of 10 or 20 wt % oligomers (PETMP-HDDI: aliphatic or TEMP-BDI: aromatic). The filler used in this composition was comprised of 85 wt % Barium glass and 15 wt % colloidal silica (OX-50), added at 75 wt % of the total mass of the composite.

Disclosed herein are dental resin composite compositions that involve the use of oligomeric additives, particularly those based on thio-urethanes (Li H et al, *Macromolecules* 42, 6537-6542 (2009); incorporated by reference herein). These are similar to compositions used in the development of polymer coatings. Results show that oligomeric thiourethane additives not only result in a resin with 50 to 75% less stress, but, in addition result in up to 95% conversion. Currently available dental resin composites result in a 60-65% conversion. Furthermore, the compositions have improved durability over currently available composites because some of the water labile ester bonds of currently available composites are replaced by thio-urethanes.

Polyurethanes and poly-thiourethane networks in the disclosed composite have the advantages of hydrogen bonding reinforcement, homogeneous network formation, and improved toughness resulting from the thiourethane bond (Senyurt A F et al, *Macromolecules* 40, 3174-3182 (2007) and Li H B, *Macromolecules* 42, 6537-6542 (2009).

The disclosed compositions also have improved mechanical reinforcement relative to currently available composites (Carioscia J A et al, *J Polymer Sci Part A—Polymer Chemistry* 45, 5686-5696 (2005) and Moraes R R et al, *Dental Materials* 27, 509-519 (2011); both of which are incorporated by reference herein). Finally, thio-urethanes have excellent optical clarity, having been successfully applied as contact lenses (U.S. Pat. No. 7,767,779; incorporated by reference herein). As a result, aesthetically improved composites can be created by tailoring the refractive index to match that of inorganic fillers added to the composite.

Pre-polymerized oligomeric additives, readily miscible with methacrylates are contemplated. Such oligomeric additives significantly reduce stress and increase conversion due to delayed gelation. Delayed gelation results from by chain-transfer reactions of pendant thiol functionalities to the methacrylate on the secondary network (Pfeifer C S et al, *Polymer* 52, 3295-3303 (2011); incorporated by reference herein) resulting in the covalent attachment of the additives to the matrix. At the same time, these oligomeric additives provide improved mechanical properties (especially toughness), more homogeneous networks and improved optical match with the inorganic filler. This approach will not require any modification on the current operatory technique, which greatly decreases the bench-to-chair-side time for implementation.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms ($C_{1-6}$alkyl). The term "alkyl" also includes cycloalkyl. The alkyl group may be a "substituted alkyl" wherein one or more hydrogen atoms are substituted with a substituent such as halogen, cycloalkyl, alkoxy, amino, hydroxyl, aryl, or carboxyl.

The term "aryl" refers to any carbon-based aromatic group including, but not limited to, benzene, naphthalene, phenyl, and oxazole. The term "aryl" also includes heteroaryl, which is defined as an aromatic group that has at least one heteroatom incorporated within the ring of the aromatic group. Heteroaryl is also termed 'heterocycle' herein. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ether, ketone, aldehyde, hydroxy, carboxylic acid, cyano, amido, haloalkyl, haloalkoxy, or alkoxy, or the aryl group can be unsubstituted.

"Heterocycle" means any optionally substituted saturated, unsaturated or aromatic cyclic moiety wherein said cyclic moiety contains at least one heteroatom selected from at least one of oxygen (O), sulfur (S), phosphorus (P) or nitrogen (N). Heterocycles may be monocyclic or polycyclic rings. Exemplary substituents include halogen, alkyl, halogenated $C_{1-6}$alkyl, alkoxy, halogenated $C_{1-6}$alkoxy, amino, amidino, amido, azido, cyano, guanidino, hydroxyl, nitro, nitroso, urea, $OS(O)_2R$, $OS(O)_2OR$, $S(O)_2OR$, $S(O)O_2R$, or $C(O)OR$ wherein R may be H, alkyl, aryl or any 3 to 10 membered heterocycle; $OP(O)OR_1OR_2$, $P(O)OR_1OR_2$, $SO_2$, $NR_1R_2$, $NR_1SO_2R_2$, $C(R_1)NR_2$, $C(R_1)NOR_2$, wherein $R_1$ and $R_2$ may be independently H, alkyl, aryl or 3 to 10 membered heterocycle; $NR_1C(O)R_2$, $NR_1C(O)OR_2$, $NR_3C(O)NR_2R_1$, $C(O)NR_1R_2$, $OC(O)NR_1R_2$, wherein $R_1$, $R_2$ and $R_3$ are each independently selected from H, alkyl, aryl or 3 to 10 membered heterocycle, or $R_1$ and $R_2$ are taken together with the atoms to which they are attached to form a 3 to 10 membered heterocycle.

Exemplary substituents of a heterocycle further include halogen (Br, Cl, I or F), cyano, nitro, oxo, amino, alkyl (e.g., $CH_3$, $C_2H_5$, isopropyl, etc.); alkoxy (e.g., $OCH_3$, $OC_2H_5$, etc.); halogenated alkyl (e.g., $CF_3$, $CHF_2$, etc.); halogenated alkoxy (e.g., $OCF_3$, $OC_2F_5$, etc.); COOH, COO-alkyl, CO-alkyl, alkyl-S (e.g., $CH_3S$, $C_2H_5S$, etc); halogenated alkyl-S(e.g., $CF_3S$, $C_2F_5S$, etc.); benzyloxy and pyrazolyl.

Exemplary heterocycles include, but are not limited to, azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

EXAMPLES

The following examples are illustrative of disclosed methods. In light of this disclosure, those of skill in the art will recognize that variations of these examples and other examples of the disclosed method would be possible without undue experimentation.

Example 1

Methacrylamide and Methacrylate Monomers for Dental Composites

Scheme 1: Preparation of aromatic methacrylamides:

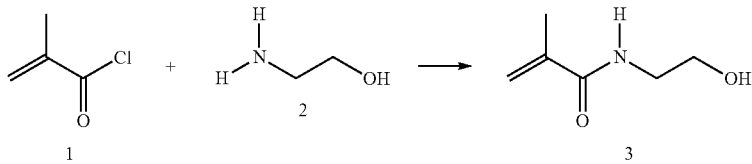

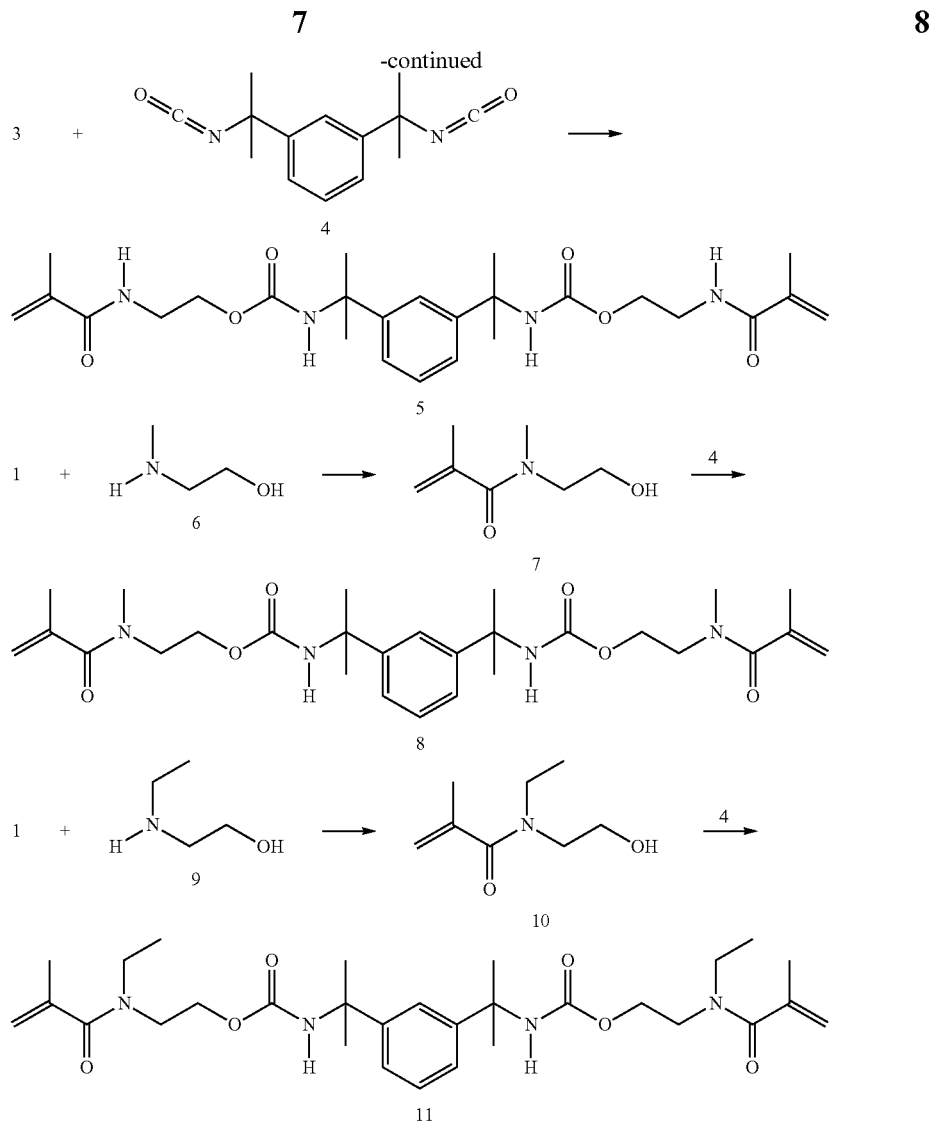

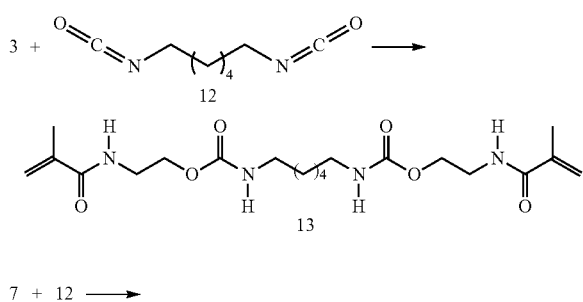

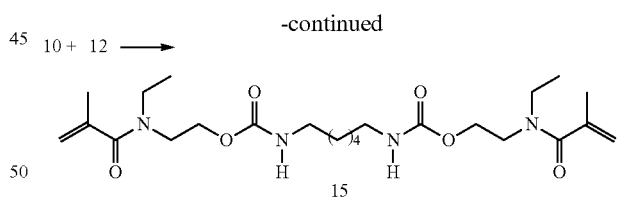

Synthesis:

Compound 5 is prepared according to Scheme 1 above. A total of 1 mole of methacryloyl chloride (compound 1) is added to 1 mole of 2-hydroxyethylamine (compound 2). These are allowed to react in a round bottomed flask in anhydrous chloroform for three hours. Solvent is removed by rotary evaporation. The result of the reaction is compound 3. Then 2 moles of compound 3 are added to 1 mole of 1, 3-bis(1-isocyanato-1-methylethyl)benzene (compound 4) in a round bottom flask in anhydrous chloroform in the presence of a catalytic amount of dibutyltin dilaurate. These are allowed to react for three hours to form compound 5. Solvent is eliminated by rotary evaporation.

Compound 8 is prepared according to Scheme 1 above. A total of 1 mole of methacryloyl chloride (compound 1) is added to 1 mole of methyl-2-hydroxyethylamine (compound 6). These are allowed to react in a round bottomed flask in anhydrous chloroform for three hours. Solvent is removed by rotary evaporation. The result of the reaction is compound 7. Then 2 moles of compound 7 are added to 1 mole of 1, 3-bis(1-isocyanato-1-methylethyl)benzene (compound 4) in a round bottom flask in anhydrous chloroform in the

Example 2

Monomer Synthesis—Sterically Hindered Methacrylates

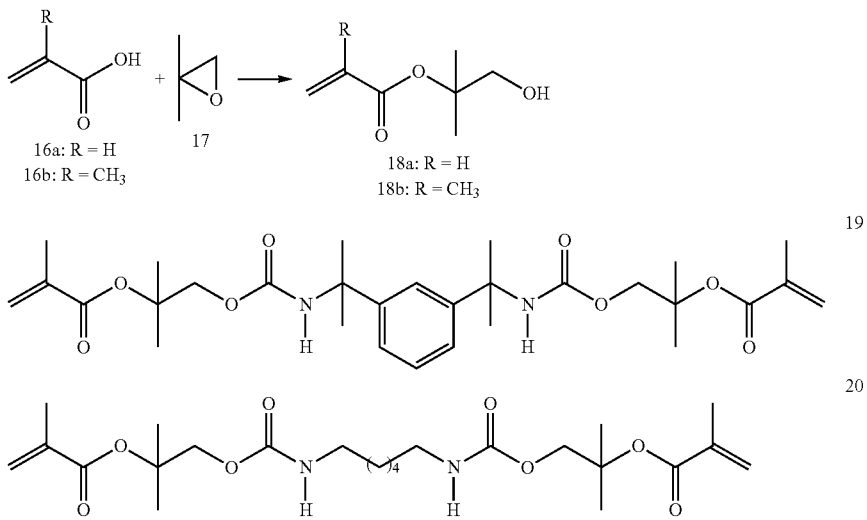

presence of a catalytic amount of dibutyltin dilaurate. These are allowed to react for three hours to form compound 8. Solvent is eliminated by rotary evaporation.

Compound 11 is prepared according to Scheme 1 above. A total of 1 mole of methacryloyl chloride (compound 1) is added to 1 mole of ethyl-2-hydroxyethylamine (compound 9). These are allowed to react in a round bottomed flask in anhydrous chloroform for three hours. Solvent is removed by rotary evaporation. The result of the reaction is compound 10. Then 2 moles of compound 10 are added to 1 mole of 1, 3-bis(1-isocyanato-1-methylethyl)benzene (compound 4) in a round bottom flask in anhydrous chloroform in the presence of a catalytic amount of dibutyltin dilaurate. These are allowed to react for three hours to form compound 11. Solvent is eliminated by rotary evaporation.

Compound 13 can be prepared according to Scheme 2 above. Compound 3 (prepared as described above) is added to 1,6-hexanediol diisocyanate (compound 12) in a round bottom flask in anhydrous chloroform in the presence of a catalytic amount of dibutyltin dilaurate. These are allowed to react for three hours to form compound 13. Solvent is eliminated by rotary evaporation.

Compound 14 can be prepared according to Scheme 2 above. Compound 7 (prepared as described above) is added to 1,6-hexanediol diisocyanate (compound 12) in a round bottom flask in anhydrous chloroform in the presence of a catalytic amount of dibutyltin dilaurate. These are allowed to react for three hours to form compound 14. Solvent is eliminated by rotary evaporation.

Compound 15 can be prepared according to Scheme 2 above. Compound 10 (prepared as described above) is added to 1,6-hexanediol diisocyanate (compound 12) in a round bottom flask in anhydrous chloroform in the presence of a catalytic amount of dibutyltin dilaurate. These are allowed to react for three hours to form compound 15. Solvent is eliminated by rotary evaporation.

Compound 19 is prepared according to Scheme 3:
A total of 1 mol of 2-propenoic acid (compound 16a) or 2-methyl-2-propenoic acid (compound 16b) is combined with 1 mol of methyl epoxide (compound 17) to a round bottom flask in anhydrous chloroform and allowed to react for 3 h hours. The reaction yields compound 18a (if 16a is used) or compound 18b (if 16b is used.) Solvent is removed using rotary evaporation.

Then 2 mols of compound 18 (18b is shown in Scheme 3) are added to 1 mole of compound 4 in a round bottom flask in anhydrous chloroform in the presence of the dibutyltin dilaurate catalyst. The compounds are allowed to react for 3 hours at room temperature and compound 19 is produced. Solvent is removed using rotary evaporation.

Compound 20 is prepared according to Scheme 3:
A total of 2 mols of compound 18 produced as described above (18b is shown in Scheme 3) are added to 1 mole of compound 12 in a round bottom flask in anhydrous chloroform in the presence of the dibutyltin dilaurate catalyst. The compounds are allowed to react for 3 hours at room temperature and compound 20 is produced. Solvent is removed using rotary evaporation.

Example 3

Monomer Synthesis—Norbornene/Methacrylamide Hybrid

Scheme 4:

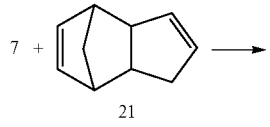

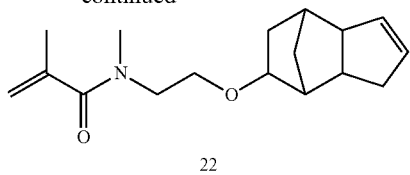

22

Compound 22 is prepared according to scheme 4. A total of 1 mole of compound 7 (that can be prepared as described above) is added to one mole of compound 21 in a round bottom flask in the presence of a catalytic amount of Cu(II) triflate catalyst. These are allowed to react for three hours to produce compound 22. Solvent is removed using rotary evaporation.

Example 4

Synthesis of Thiourethane Oligomers

Isocyanates and thiols can be reacted to form thio-urethane networks. These networks, when added to dental matrices result in improved toughness, a high refractive index, and optical clarity. The Flory-Stockmeyer equation can be used to select starting amounts of isocyanates and thiols to result in pendant isocyanate or thiol functional groups available to be functionalized with a hydroxyl terminated methacrylamide (such as those derived from compounds 5, 8, 11, 13, 14, 15, 19, and 20 described herein).

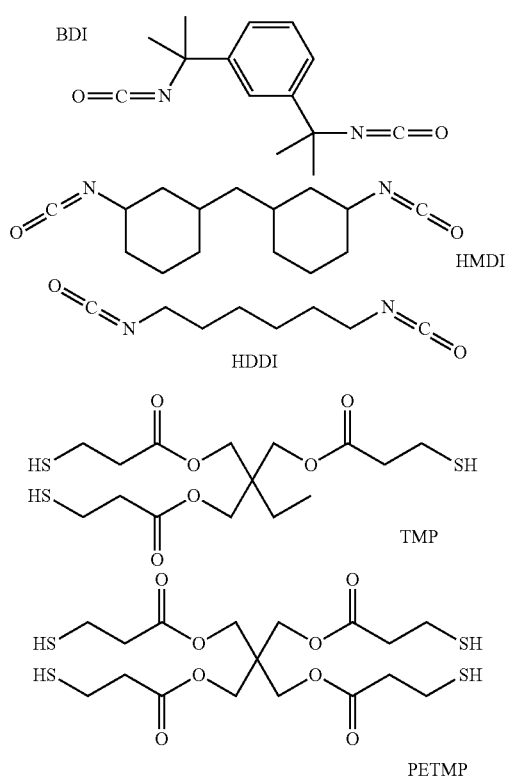

In one example, a thiol terminated thiourethane oligomer is produced when an excess of thiol compound (for example TMP or PETMP above) is added to an isocyanate compound (for example BDI, HMDI, or HDDI above). For example, 5 g of one or more of the above thiol compounds is added to 1.8 g of one of the above isocyanate compounds in a two neck round bottom flask at room temperature. A mid-IR spectrum can be taken at this point. The flask is purged with $N_2$ gas for one hour. A catalytic amount of triethyl amine is added. The flask is again purged with $N_2$ gas for 10 minutes and immersed in an ice bath for four hours. A second mid-IR spectrum can be taken at this point. The isocyanate peak at 2270 $cm^{-1}$ will be reduced (potentially to zero) if the reaction is complete. The resulting mixture is added drop wise to a volume of hexane that is 4× the volume of the mixture. This is allowed to separate at least 4 hours. The supernatant is discarded and the product is resuspended in dry acetone. Solvent is removed with rotary evaporation.

In a second example, an isocyanate-terminated thiourethane oligomer is produced when an excess of isocyanate compound (for example BDI, HMDI, or HDDI above) is added to a thiol compound (for example TMP or PETMP above). For example, 5 g of one or more of the above isocyanate compounds is added to 2 g of one or more of the above thiol compounds in a two neck round bottom flask at room temperature. A mid-IR spectrum can be taken at this point. The flask is purged with $N_2$ gas for one hour. A catalytic amount of triethyl amine is added. The flask is again purged with $N_2$ gas for 10 minutes and immersed in an ice bath for four hours. A second mid-IR spectrum can be taken at this point. The isocyanate peak at 2270 $cm^{-1}$ will be reduced (potentially to zero) if the reaction is complete. The resulting mixture is added drop wise to a volume of hexane that is 4× the volume of the mixture. This is allowed to separate at least 4 hours. The supernatant is discarded and the product is resuspended in dry acetone. Solvent is removed with rotary evaporation.

Example 5

Methacrylamide Composites

An exemplary methacrylamide composite composition can include a resin complex comprising 10%-90% compound 8 and/or compound 11 and 10%-90% compound 14 and/or compound 15. This is added to 0.2% by weight of camphorquinone and 0.8% by weight of ethyl-4-methylamino benzoate.

A filler comprising a total of 0-80% by weight of the total composite mass is also added. The filler portion itself is composed of 85% by weight of silanated barium borosilicate glass (0.4-0.7 μm) and 15% by weight of silane treated aerosol silica.

The thiourethane oligomer described in Example 4 above is added at 5-30% by weight.

All these elements are mixed together using a FlackTek Inc SpeedMixer™ operated at 2700 rpm for 5 min, to form the light-sensitive paste of composite.

Example 6

Methacrylate/Norbornene Composites

An exemplary methacrylate/norbornene composite composition can comprise: A resin complex comprising 10%-90% compound 19 and/or compound 22 and 10%-90% compound 20. This is added to 0.2% by weight of camphorquinone and 0.8% by weight of ethyl-4-methylamino benzoate.

A filler comprising a total of 0-80% by weight of the total composite mass is also added. The filler portion itself is composed of 85% by weight of silanated barium borosilicate glass (0.4-0.7 μm) and 15% by weight of silane treated aerosol silica.

The thiourethane oligomer described in Example 4 above is added at 5-30% by weight.

All components are mixed together using a FlackTek Inc SpeedMixer™ operated at 2700 rpm for 5 min, to form the light-sensitive paste of composite.

Example 7

Thiourethanes Improve the Mechanical Properties of Light-cured Resin Cements

Bonded indirect restorations play one of the major roles in contemporary dentistry. Resin cements have become popular clinically because of their ability to bond both to the tooth structure and to the restoration (Peumans M et al, *J Dent* 28, 163-177 (2000); Manso A P et al, *Dent Clin North Am* 55, 311-332 (2011); both of which are incorporated by reference herein). Examples of their clinical applications include adhesion of ceramic fragments, crowns, bridges, and intra-canal posts. Due to the necessary (and sometimes excessive) taper on tooth preparations, and to constant incidence of tensile, compressive and oblique loads, resin cements must have resistance to dissolution, strong bond to structures and high mechanical properties (Meyer J M et al, *Biomaterials* 19, 529-539 (1998); Rosenstiel S F et al, *J Prosthet Dent* 80, 280-301 (1998); Manso et al, 2011 supra); all of which are incorporated by reference herein. Conventional resin cements are based on methacrylate monomers which undergo vitrification at early stages of polymerization, increasing the strain/stress at the bonded interface and in the bulk of the material structure. This condition increases the risk of gap formation at the interface of cementation, which may lead to an increase of the material solubility, microleakage and staining, ultimately compromising the longevity of treatment. Based on the confined geometry in which the cement is applied, current operatory techniques available are not efficient in avoiding the development of strain/stress during the indirect restoration placement and, therefore, the solution to minimize stress generation needs to be based on improvements made directly to the material (Braga R R et al, *J Dent* 30, 333-340 (2002); incorporated by reference herein).

The use of thiol-enes has been proposed in dental composites, with successful results as stress reducing agents. The step growth nature of the thiol-ene and thiol-methacrylate polymerizations, given by chain-transfer reactions of the thiol to the ene/vinyl, lead to more homogeneous network formation and ultimately increased conversion in comparison to the pure methacrylate counterparts and for selected compositions, improvements in flexural strength, depth of cure and water solubility have also been reported (Lu H et al, *Dent Mater* 21, 1129-1136 (2005); Cramer N B et al, *Dent Mater* 26, 21-28 (2010); Cramer N B et al, *Dent Mater* 26, 799-806 (2010); Boulden J E et al, *Dent Mater* 27, 267-272 (2011); all of which are incorporated by reference herein). However, concerns over the somewhat compromised mechanical properties and the stability (shelf-life) of the fully formulated composite materials have delayed the commercial translation of thiol-ene-based materials (Beigi S et al, *Dent Mater* 29, 777-787 (2013); incorporated by reference herein). Another concern that applies to small molecule thiols is the foul odor associated with the material.

As an alternative to conventional thiol-enes or thiol-methacrylates, others have proposed the use of thiourethane networks in applications where mechanical properties in general, but more specifically toughness and resistance to impact, are desirable. Several studies have demonstrated the more homogeneous nature of thiourethane networks compared to the simple urethane counterparts, as well as the increased toughness values (Senyurt A F et al, *Macromolecules* 40, 3174-3182 (2007) and Li Q et al, *J Polymer Sci Part A Polymer Chem* 45, 5103-5111 (2007); both of which are incorporated by reference herein). In those studies, thiols are combined with isocyanates in situ, in a reaction catalyzed by a base. Currently, these are two-part systems not suitable for dental composite applications. However, previous studies have demonstrated it to be possible to synthesize high molecular weight pre-polymerized thiourethane oligomers to be later added to a secondary monomer matrix, polymerizable through a radical mechanism (Pfeifer C et al, https://iadr.confex.com/iadr/43am/webprogram/Paper186849.html; incorporated by reference herein). When the oligomer is designed to have pendant thiols from the backbone, chain-transfer reactions to the surrounding methacrylate matrix result in delayed gelation and vitrification and, as consequence, reduction in polymerization stress. Due to the high molecular weight, reductions in the volumetric shrinkage are also expected, as well as the elimination of the odor concerns. Importantly, thiol-terminated thiourethanes are capable of forming a more homogeneous network with the methacrylate, and also increase final conversion (Berchtold K A et al, *Macromolecules* 35, 7968-7975 (2002); incorporated by reference herein).

Therefore, the objectives of this study are to synthesize examples of thiol-terminated thiourethane oligomers with different backbone structures and to assess the properties of a methacrylate-based resin cement modified with the oligomers. The hypotheses of this study were that the use of thiourethanes would (I) increase the degree of conversion, (II) reduce the volumetric shrinkage/polymerization stress and (III) improve the material mechanical properties.

Materials: The experimental resin cement formulated for the study (BUT) was composed of Bis-phenol A diglycidyl dimethacrylate (Bis-GMA; Esstech, Essington, Pa., USA), urethane dimethacrylate (UDMA; Esstech) and tri-ethylene glycol dimethacrylate (TEGDMA; Esstech) in a 50:30:20 mass ratio. This is interchangeably referred to as "experimental cement" or "BUT materials" herein. Photoinitiators were added to the matrix as follows: 0.6 wt % of a tertiary amine (EDMAB—ethyl 4-dimethylaminobenzoate; Avocado, Heysham, England), 0.2 wt % of dl-camphoroquinone (Polysciences Inc., Warrington, Pa., USA), and 0.5 wt % inhibitor (BHT—2,6-di-tert-butyl-4-methylphenol; SigmaAldrich, St. Louis, Mo., USA).

Oligomers were synthesized in solution (methylene chloride) by combining 1,6-Hexanediol-diissocyante (aliphatic) or 1,3-bis(1-isocyanato-1-methylethyl)benzene (aromatic) with pentaerythritol tetra-3-mercaptopropionate (PETMP) (with a total of four thiol groups) or trimethylol-tris-3-mercaptopropionate (TMP) (with a total of three thiol groups), at a 1:2 isocyanate:thiol molar ratio, leaving pendant thiols. Triethylamine was used as a base in catalytic amounts. Oligomers were purified by precipitation in hexanes and rotaevaporation, then characterized by $^1$H-NMR and mid-IR spectroscopy. Thio-urethane oligomers were added to organic matrix in proportions of 0 (control), 10, 20 and 30 wt %. Filler was introduced at 25 wt% (15% OX-50 colloidal silica—0.04 mm; 85% Barium glass 0.7 μm, density 3.0 g/ml, refractive index 1.553—V117

4107, Esstech), with the aid of a mechanical mixer (DAC 150 SpeedMixer™, FlackTek Inc, Landrum, S.C., USA) for 5 min at 2400 rpm. All procedures were carried out under safe yellow light.

One commercial light-cured cement (RelyX Veneer, 3M Espe, St. Paul, USA—lot N521803; Ref 7614A1, A1/light yellow shade) composed by BisGMA/TEGDMA and 66 wt % zirconia/silica filler was modified by addition of 10 and 20 wt % of aromatic oligomer to organic matrix.

Photopolymerization reaction kinetics and degree of conversion: The degree of conversion (DC) was obtained using near-infrared (NIR) spectroscopy in specimens of 10 mm in diameter and 0.8 mm thick laminated between two glass slides, based on the methacrylate =$CH_2$ absorption at 6165 cm$^{-1}$ (Stansbury J W and Dickens S H, *Dent Mater* 17, 71-79 (2001); incorporated by reference herein) before and after 60 s of irradiation at 700 mW/cm$^2$ (Bluephase, Ivoclar vivadent, Lichtenstein) with the light source in direct contact with the glass slide mold. Real-time monitoring of the polymerization kinetics was carried out in specimens of the same size at 2 scans per spectrum with 4 cm$^{-1}$ resolution, which provides a greater than 2 Hz data acquisition rate. Kinetic data was collected continuously for 5 min. Samples (n=3) were irradiated for 60 s with a LED lamp at an incident irradiance of 550 mW/cm$^2$. The light attenuation in this case was due to a distance of 2 cm separating the tip of the light guide and the surface of the specimen.

Flexural strength, elastic modulus and toughness: Flexural strength of the samples was measured according to the 3-point bending method carried out with a universal test machine (Q-test, MTS, Eden Prairie, Wis.) at a cross-head speed of 0.5 mm min$^{-1}$. The bar specimens were prepared in dimensions of 2 mm×2 mm×25 mm according to ISO 4049. The specimens (n=10) were fabricated between glass slides and photopolymerized with three overlapping 60 s exposures at 700 mW/cm$^2$. Specimens were stored for one week in dark containers at room temperature. The flexural strength (FS) in MPa was then calculated as:

$$FS(\sigma) = \frac{3Fl}{2bh^2}$$

where F stands for load at fracture (N), l is the span length (20 mm), and b and h are the width and thickness of the specimens in mm, respectively. The elastic modulus was determined from the slope of the initial linear part of stress-strain curve.

$$E = \frac{Fl^3}{4bh^3d}$$

F=the load at some point on the linear region of the stress-strain curve
d=the slack compensated deflection at load F
l, b, and h are as defined above Toughness was calculated in MPa from the integration of the stress×strain curve using software (Origin 9.1, OriginLab Corporation, Northampton, Mass., USA).

Volumetric Shrinkage: The bonded disk method was used to evaluate volumetric shrinkage. Resin cements were placed into a brass ring of approximately 16 mm in diameter and 1.5 mm in height bonded to a glass slide. The cement (n=5) was placed so that it did not come in contact with the brass ring, and then the assembly was covered with a microscope cover slip (approximately 0.1 mm thick). A linear variable differential transducer (LVDT) probe was placed in contact with the center of the cover slip. The cement was photoactivated for 60 s at an incidence of 650 mW/cm$^2$. As the cement cures and shrinks, it pulls the cover slip down and its deflection is monitored by the LVDT probe. Displacement data was obtained from the signal output of the transducer (in mV). The volumetric shrinkage (% VS) value was calculated as follows:

$$\% VS = \frac{(V_f - V_i) \times 2}{h} \times 100$$

Where: $V_f$ is the final displacement value given after polymerization and, $V_i$, is the initial value given by the LVDT probe, in mV and h, is the cement specimen thickness after the polymerization, in µm.

Polymerization stress: Polymerization stress development was followed in real-time using the Bioman, described previously (Watts D C and Satterthwaite J D, *Dent Mater* 24, 1-8 (2008); incorporated by reference herein. This system consists of a cantilever load cell whose extremity is fitted to a rigid integral clamp on its free end. The clamp holds a 10 mm diameter and 22 mm tall steel rod vertically and perpendicular to the load cell axis. A 5-mm diameter, 0.5-mm tall steel rod was fixed at the center of the lower face of the standard rod with a cyanoacrylate adhesive to produce a rod substrate with a reduced surface area to be consistent with a C-factor of 4. The surface of the rod was treated with a thin layer of Metal primer (Z-prime plus, Bisco, Schaumburg, Ill.). The opposite surface was a rigid fused silica glass plate of 3 mm thickness, treated with a thin layer of silane ceramic primer (3M ESPE, St. Paul, Minn., USA). The cement (n=5) was then inserted into the 0.5-mm gap between the upper rod and the lower glass slide and shaped into a cylinder. The specimens were photoactivated through the glass during 60 s at an incident irradiance of 300 mW/cm$^2$ (Bluephase) and the stress followed for 500 s. The load signal from the cantilever cell was amplified and acquired by a computer.

Fracture toughness: The fracture toughness of all materials was determined from the stress intensity factor (K) during crack propagation in the elastic region. To determine the fracture toughness (FT), single-edge notch beam (SENB) specimens (n=5) were fabricated according to ASTM Standard E399-90 [35-beigi] in a 5 mm×2 mm×25 mm split steel mold with a razor blade providing a 2.5 mm notch in the center of the specimens. The cement was photoactivated for 60 s at an incidence of 700 mW/cm$^2$. The bending fracture test was performed at a cross-head speed of 0.5 mm min$^{-1}$ using a universal test machine (Q-test) and the fracture toughness (critical stress intensity factor, $K_{IC}$) was calculated according the following equation:

$$K_{IC} = \frac{3PL}{2BW^{3/2}} \left\{ 1.93\left(\frac{a}{W}\right)^{1/2} - 3.07\left(\frac{a}{W}\right)^{3/2} + 14.53\left(\frac{a}{W}\right)^{5/2} - 25.11\left(\frac{a}{W}\right)^{7/2} + 25.8\left(\frac{a}{W}\right)^{9/2} \right\}$$

where P is load at fracture (N), L, W, B, and α are length, width, thickness, and notch length (in mm), respectively. The span length and load cell capacity were 20 mm and 60

N, respectively. The subscript IC denotes mode 1 crack opening under a normal tensile stress perpendicular to the crack.

Statistical analysis: For the experimental cement, statistical analysis was carried out by two-way ANOVA (thio-urethane concentration and thio-urethane type) in the tests of degree of conversion, $Rp_{max}$, conversion at vitrification, flexural strength, flexural modulus and toughness. One-way ANOVA was performed for the experimental cement in the tests of polymerization stress, volumetric shrinkage and fracture toughness, and for all tests of commercial cements, once they used only aromatic oligomers. Multiple comparisons were done using Tukey's test ($\alpha=0.05\%$).

tration of added thiourethane (p=0.004). No interaction between the two factors was observed for $Rp_{max}$ (p=0.188). All values are presented in Table 1.

The conversion at $Rp_{max}$ was used as a measure of network vitrification as shown in Table 1. Even though there were statistical differences between some groups (p=0.035), all experimental groups presented results statistically similar to the control. Therefore, the presence of thio-urethane significantly influenced the vitrification results, while the thio-urethane type showed to be not statistically significant (p=0.693). There was interaction between the factors (p=0.028).

TABLE 1

Degree of conversion, maximum rate of polymerization ($Rp_{max}$) and conversion at vitrification for experimental cements. Values followed by the same superscript within the same test are statistically similar ($\alpha$ = 5%).

|  | Degree of conversion (%)* | | $Rp_{max}$ (% · s$^{-1}$)** | | Vitrification (%)** | |
| --- | --- | --- | --- | --- | --- | --- |
|  | aromatic | aliphatic | aromatic | aliphatic | aromatic | aliphatic |
| control | 64.87 (0.44)$^d$ | | 4.5 (0.6)$^a$ | | 15.7 (1.1)$^{ab}$ | |
| 10% | 64.8 (0.3)$^d$ | 66.2 (0.3)$^c$ | 2.2 (0.3)$^b$ | 1.7 (0.1)$^{b,c}$ | 13 (1.8)$^{ab}$ | 11.6 (1.6)$^b$ |
| 20% | 63.6 (0.4)$^e$ | 69.4 (0.3)$^b$ | 2.1 (0.1)$^{b,c}$ | 1.2 (0.0)$^c$ | 11.8 (1.5)$^b$ | 17.7 (3.8)$^a$ |
| 30% | 64.9 (0.4)$^d$ | 73.5 (0.3)$^a$ | 1.6 (0.1)$^c$ | 1.2 (0.2)$^c$ | 18.2 (2.2)$^a$ | 15.2 (4.1)$^{ab}$ |

*obtained from photoactivation with the light guide in direct contact with the sample
**obtained from samples photoactivated in an IR chamber Photo Polymerization Reaction Kinetics and Degree of Conversion:

Experimental cement: The degree of conversion (Table 1) in experimental cements comprising aliphatic thiourethanes was significantly higher relative to controls. The cement comprising 30% aliphatic thiourethane had 73.5±0.3% conversion while the control had 64.87±0.44% conversion (p=0.001). In experimental cements comprising aromatic thiourethanes, the degree of conversion was significantly lower. For example, the degree of conversion for the experimental cement comprising 20% aromatic thiourethane was 63.6±0.4%, while the degree of conversion of the control was 64.87±0.44% which was statistically significant. Aliphatic thio-urethanes were statistically superior to compared to aromatic thiourethanes at all concentrations tested (p=0.001). There was a statistical interaction between the two factors tested (thiourethane type and concentration—p=0.001).

Figure 5:
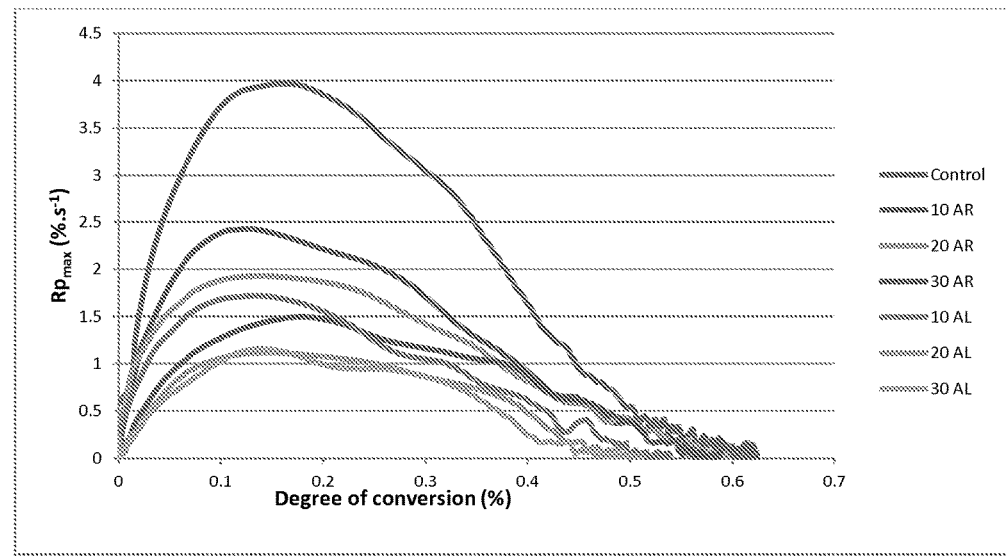
FIG. 5 is a line graph depicting the degree of conversion as a function of rate of polymerization for BisGMA/UDMA/TEGDMA dental cement comprising aromatic (AR) or aliphatic (AL) thiourethanes at 10%, 20% or 30% by weight compared to a control cement lacking thiourethane.

A statistical reduction in the rate of polymerization ($Rp_{max}$) values was observed for all cements comprising thiourethanes relative to the control (p=0.001). For cements comprising aliphatic thiourethanes, there was no statistical difference amongst all concentrations. For cements comprising aromatic thiourethanes, $Rp_{max}$ was statistically higher in cements comprising 10% aromatic thiourethane compared to cement comprising 30% aromatic thiourethane. The 20 wt % group was statistically similar to 10 wt %. $Rp_{max}$ was also influenced by the thio-urethane type, with aromatic thiourethane groups displaying higher $Rp_{max}$ at the same concen- FIG. 5 presents the kinetic profiles of all groups formulated with BisGMA/UDMA/TEGDMA. For cements comprising 20% and 30% aliphatic thiourethanes (20 AL and 30 AL in FIG. 5) and the cement comprising 30% aromatic thiourethane (30 AR in FIG. 5), not only is the maximum rate of polymerization ($Rp_{max}$) lower than the control, but the rate of deceleration is also lower than the control. This is evidenced by the plateau in the $Rp_{max} \times DC$ curves shown in FIG. 5.

Proprietary cement: Proprietary cement is dental cement obtained from a commercial source. The exact formulation of the proprietary cement is unknown. It is also referred to herein as "commercial cement" or "commercial materials." It is known not to contain thiourethane. Proprietary cement used herein is the RelyX Veneer® cement with a thiourethane additive. Results from that preparation are presented in Table 2. Proprietary cement with 20% aromatic thio-urethane oligomer resulted in significantly higher DC relative to control (p=0.030). Proprietary cement comprising 10% aromatic thiourethane was not statistically different from the control. Furthermore, addition of thiourethane to proprietary cement resulted in a significantly lower $Rp_{max}$ than control for both 10% and 20% thiourethane. (p=0.001). A higher conversion at vitrification for the thiourethane-modified groups in relation to the control was observed (p=0.048).

TABLE 2

Mean and standard deviation for degree of conversion, maximum rate of polymerization ($Rp_{max}$), conversion at vitrification, flexural strength, flexural modulus and toughness for RelyX Veneer ® cement modified with aromatic thiourethane oligomers. Values followed by the same superscript within the same test are statistically similar ($\alpha = 5\%$).

|  | Degree of conversion (%) | $Rp_{max}$ (% · $s^{-1}$) | Vitrification (%) | Flexural strength (MPa) | Flexural modulus (MPa) | Toughness (MPa) |
|---|---|---|---|---|---|---|
| Control | 65.35 (0.16)[b] | 4.69 (0.13)[a] | 10.93 (0.50)[a] | 234 (24.86)[a] | 8061.06 (793.82)[a] | 4.76 (0.55)[a] |
| 10% | 66.77 (1.23)[ab] | 1.35 (0.34)[b] | 15.36 (1.17)[b] | 226.42 (27.89)[a] | 7097.34 (949.37)[ab] | 5.48 (0.49)[a] |
| 20% | 68.25 (1.15)[a] | 0.75 (0.03)[b] | 16.03 (3.39)[b] | 205.03 (28.03)[a] | 6428.16 (749.24)[b] | 5.5 (0.8)[a] |

Flexural Strength, Elastic Modulus and Toughness:

Experimental cement: Addition of aromatic thiourethanes to the experimental cement resulted in greater flexural strength (FS) (Table 3) relative to the control. In contrast, addition of aliphatic thiourethanes resulted in greater flexural strength only at 20% thiourethane (p=0.001). The higher flexural strength of experimental cement comprising aromatic thiourethanes was statistically higher than that of experimental cement comprising the aliphatic thiourethanes (p=0.004). There was no statistical interaction between the factors (thiourethane concentration and type) (p=0.265).

Flexural modulus of all cements comprising thiourethanes was similar to that of the control, with two exceptions. Cements with 10% added aromatic thiourethane had a significantly higher flexural modulus, while cements with 30% added aliphatic thiourethane had a significantly lower flexural modulus (p=0.001), both relative to controls (Table 3). Differences between cements with aromatic and aliphatic thiourethanes were statistically significant, with cements comprising aromatic thiourethanes having a superior flexural modulus (p=0.000). The interaction between the factors was significant (p=0.020).

With regard to toughness (Table 3), cements comprising aliphatic thiourethanes had significantly higher toughness relative to controls (p=0.001) as well as cements comprising aromatic thiourethanes at all concentrations tested. Cements comprising aromatic thiourethanes were no different than controls with regard to toughness. The interaction between the two factors was also significant (p=0.023).

Proprietary cement: A proprietary cement comprising 20% added aromatic thiourethanes had a significantly lower flexural modulus (p=0.001) relative to the proprietary cement without added thiourethanes. The cement with 10% added thiourethanes was not statistically different from the proprietary cement without added thiourethanes. No difference with regard to flexural strength (p=0.062) and toughness (p=0.104) was observed in any of the proprietary cements with or without added thiourethanes. All values are presented in Table 2 above.

Polymerization Volumetric Shrinkage

Figure 6A:
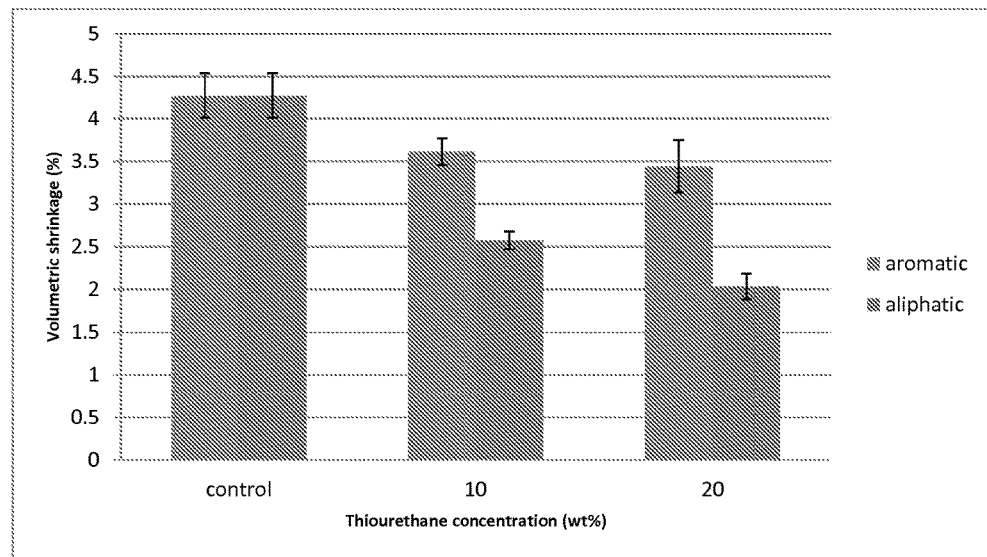
FIG. 6A is a bar graph showing the volumetric shrinkage of BisGMA/UDMA/TEGDMA dental cement comprising 10% or 20% aliphatic or aromatic thiourethane as indicated.
Figure 6B:
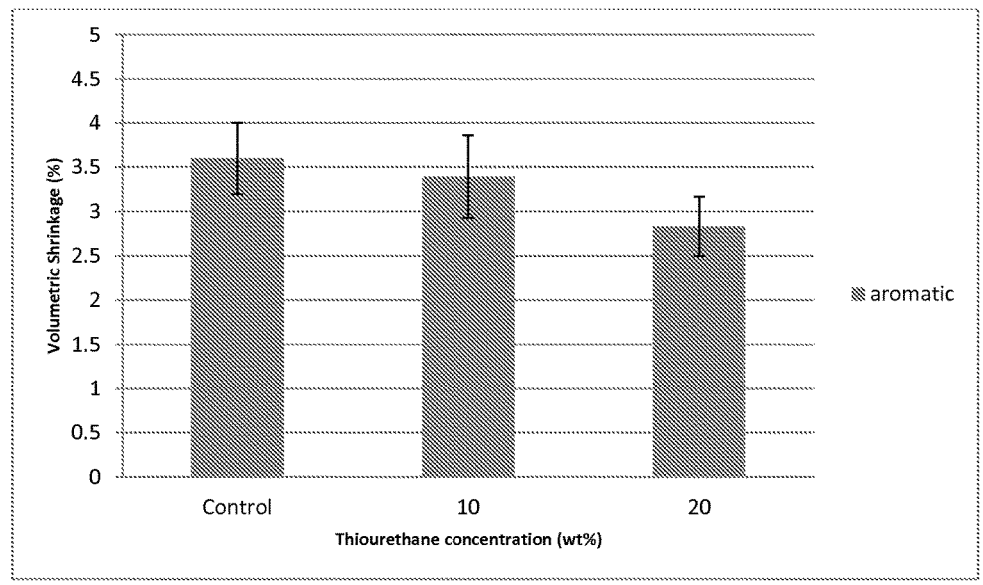
FIG. 6B is a bar graph showing the volumetric shrinkage of a proprietary dental cement (RelyX Veneer®) with 10% or 20% aromatic thiourethane as indicated.

BisGMA/UDMA/TEGDMA experimental cements containing thiourethane oligomers had significantly less volumetric shrinkage values relative to controls without added thiourethane oligomers (p=0.001) (FIG. 6A). Thiourethane type also influenced the volumetric shrinkage, with cements comprising aliphatic thiourethane oligomers having lower shrinkage values at all concentrations tested (p=0.001). Interaction between the two factors was observed (p=0.001). Cements comprising 10% and 20% added aromatic thiourethane had volumetric shrinkage 15.5% and 19.5% lower than the control, respectively. For the cements comprising 10% and 20% aliphatic oligomers, the reductions in volumetric shrinkage were, respectively, 39.8% and 52.4% in relation to the control. In the proprietary cement, the same tendency in reduction was observed in all groups with added thiourethane, although the results were not statistically significant (p=0.106) (FIG. 6B). Proprietary cements with 10%

TABLE 3

Mean and standard deviation for flexural strength, flexural modulus and toughness for the BisGMA/UDMA/TEGDMA cements modified with aromatic or aliphatic thiourethane oligomers. Values followed by the same superscript within the same test are statistically similar ($\alpha = 5\%$).

|  | Flexural strength (MPa) | | Flexural modulus (MPa) | | Toughness (MPa) | |
|---|---|---|---|---|---|---|
|  | aromatic | aliphatic | aromatic | aliphatic | aromatic | aliphatic |
| control | 90.61 (18.91)[c] | | 2020.77 (174.9)[b] | | 2.37 (0.62)[b] | |
| 10% | 108.56 (20.68)[ab] | 100.96 (15.84)[bc] | 2238.1 (266.74)[a] | 2040.83 (137.43)[ab] | 3.83 (0.78)[b] | 7.32 (1.96)[a] |
| 20% | 122.52 (12.78)[a] | 108.13 (9.84)[ab] | 2151.9 (111.38)[ab] | 2084.76 (190.91)[ab] | 3.48 (1.36)[b] | 8.21 (3.69) |
| 30% | 112.5 (8.62)[ab] | 95.28 (6.28)[bc] | 2033.6 (86.32)[b] | 1720.3 (132.71)[c] | — | — | and 20% added thiourethane resulted in a 5.6% and 21.2% reduction in shrinkage in relation to the control.

Polymerization Stress

Figure 7A:
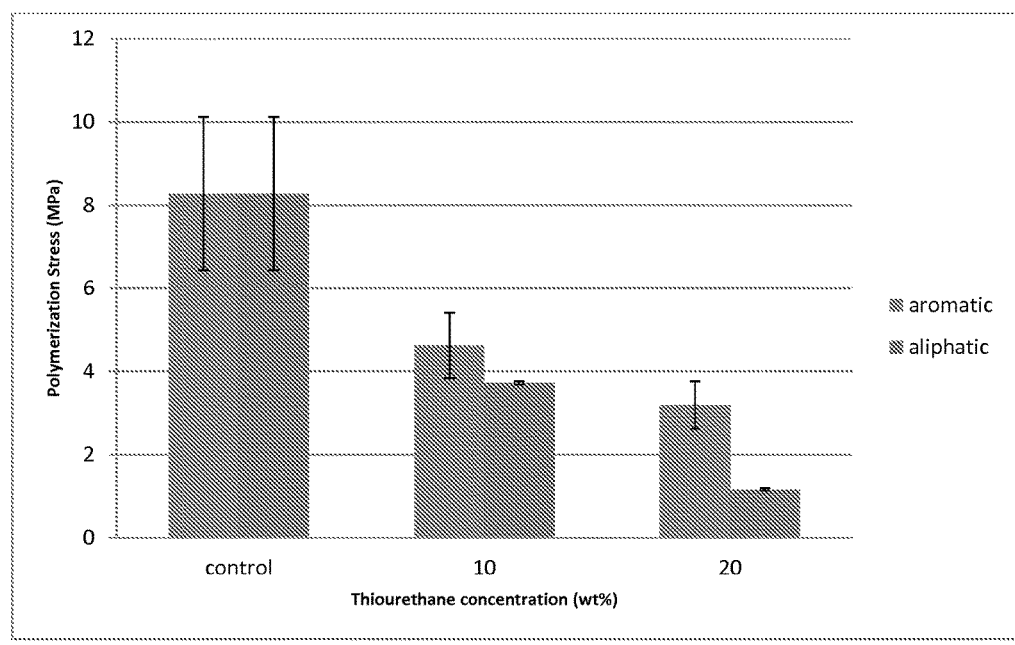
FIG. 7A is a bar graph showing the polymerization stress of BisGMA/UDMA/TEGDMA dental cement comprising 10% or 20% aromatic or aliphatic thiourethane as indicated.
Figure 7B:
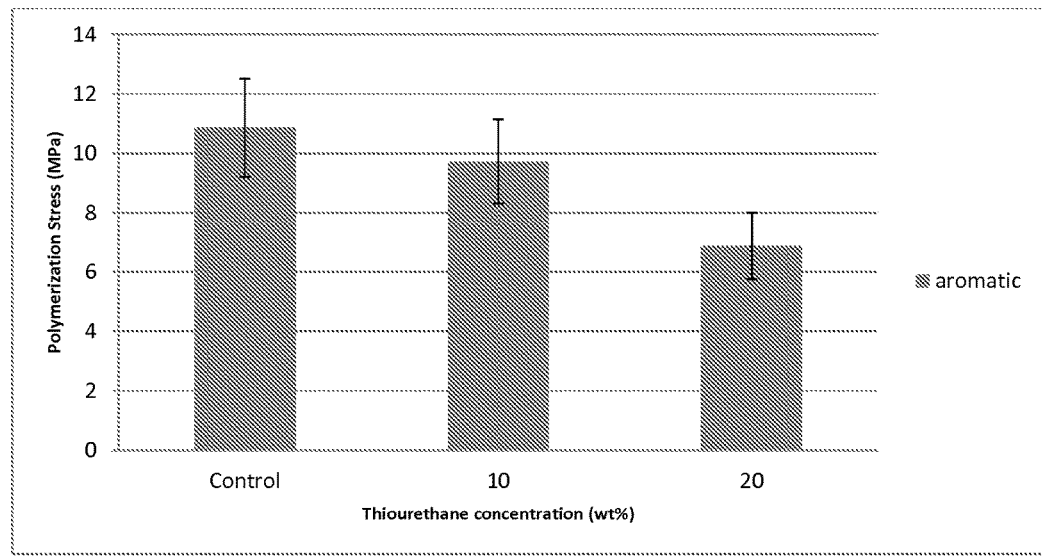
FIG. 7B is a bar graph showing the polymerization stress of RelyX Veneer® dental cement with 10% or 20% added aromatic thiourethane as indicated.

Experimental cement with added thiourethanes showed significantly less polymerization stress than controls (p=0.001). Cement with 20% of aliphatic thiourethane had the lowest value (FIG. 7A). Differences with regard to thiourethane type (p=0.120) and the interaction between the factors (0.311) were not statistically significant. Cements with 10% and 20% aromatic thiourethane oligomers resulted in polymerization stress 47.6% and 61.5%, respectively, of that of controls. Cements with 10% and 20% aliphatic thiourethane oligomers resulted in polymerization stress of 55.1% and 86%, respectively, of that of controls. The proprietary cement with 20% added aromatic thiourethane had significantly less polymerization stress (p=0.033), at 36.7% lower than the control. Proprietary cement with 10% thiourethane (FIG. 7B) was not significantly different than that of control.

Fracture Toughness

Figure 8A:
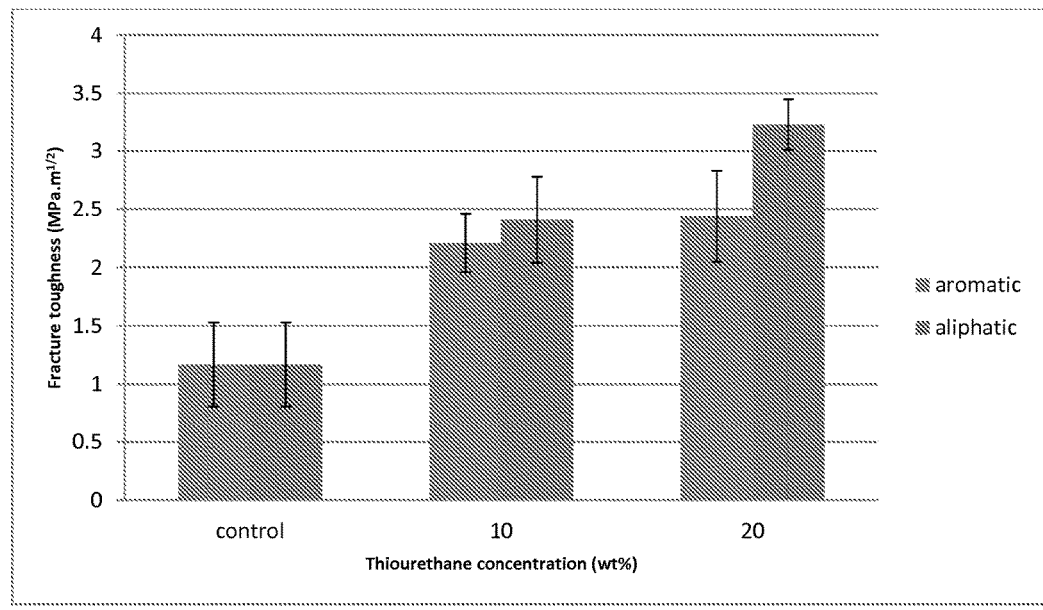
FIG. 8A is a bar graph showing the fracture toughness of BisGMA/UDMA/TEGDMA dental cement comprising 10% or 20% aromatic or aliphatic thiourethane as indicated.
Figure 8B:
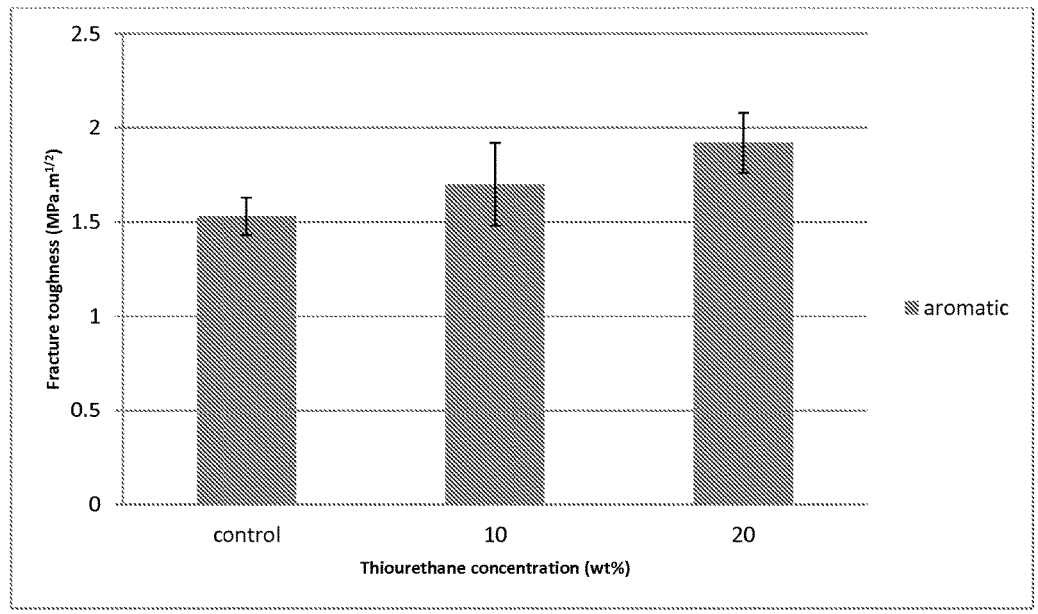
FIG. 8B is a bar graph showing the fracture toughness of RelyX Veneer® dental cement with 10% or 20% added aromatic thiourethane as indicated.
Figure 9A:
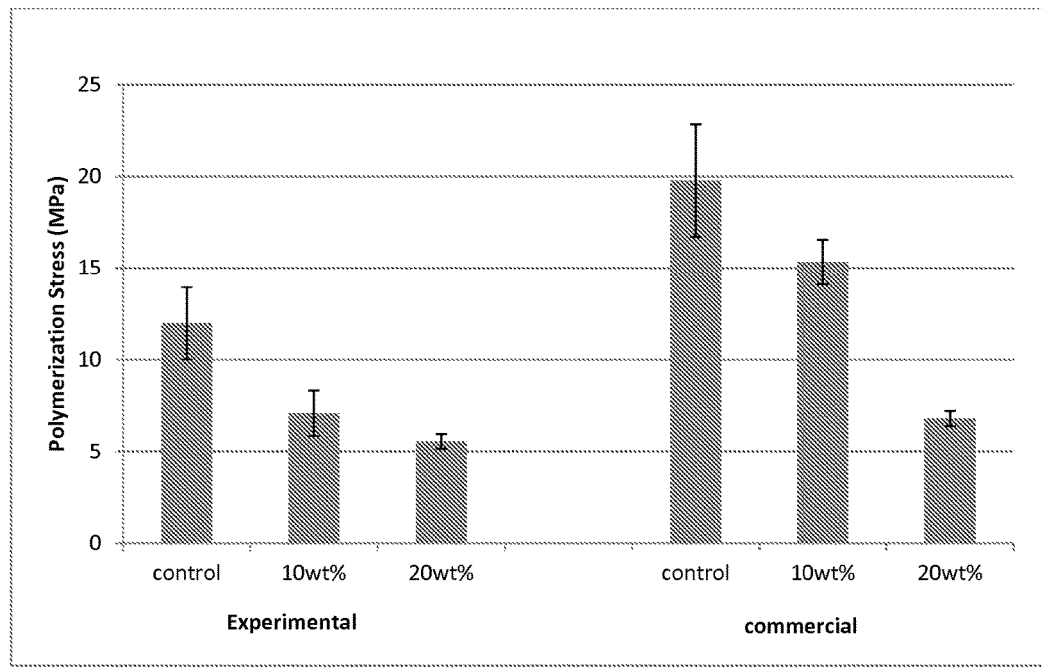
FIG. 9A is a bar graph showing the polymerization stress of BisGMA/UDMA/TEGDMA cement (experimental) and RelyX Ultimate® cement (commercial)
Figure 9B:
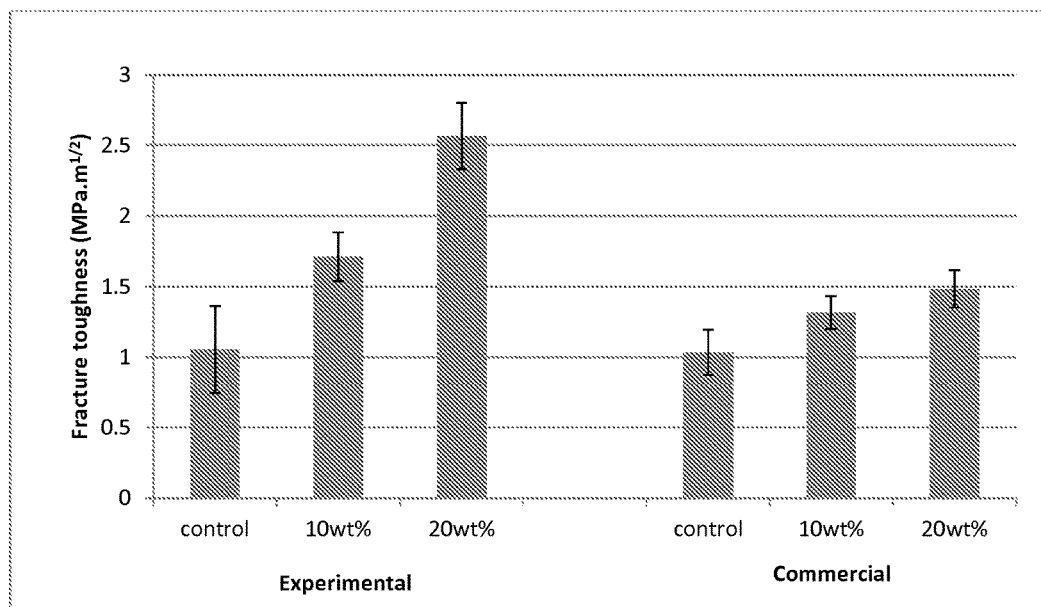
FIG. 9B is a bar graph showing the fracture toughness of BisGMA/UDMA/TEGDMA cement (experimental) and RelyX Ultimate® cement (commercial).
Figure 10A:
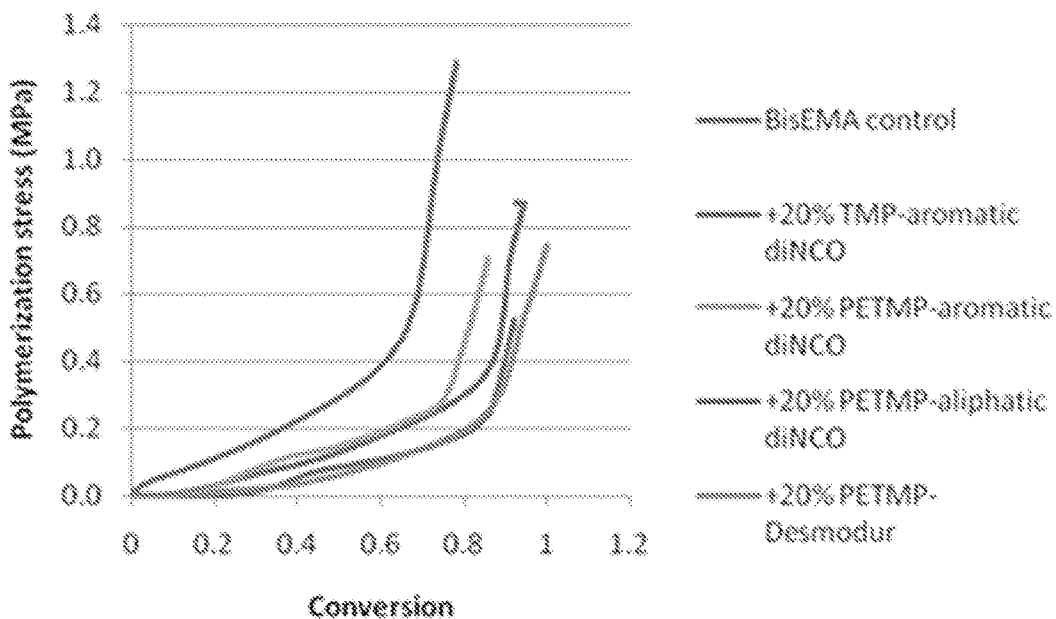
FIG. 10A is a line graph showing the polymerization stress of the indicated compositions as a function of the degree of conversion.
Figure 10B:
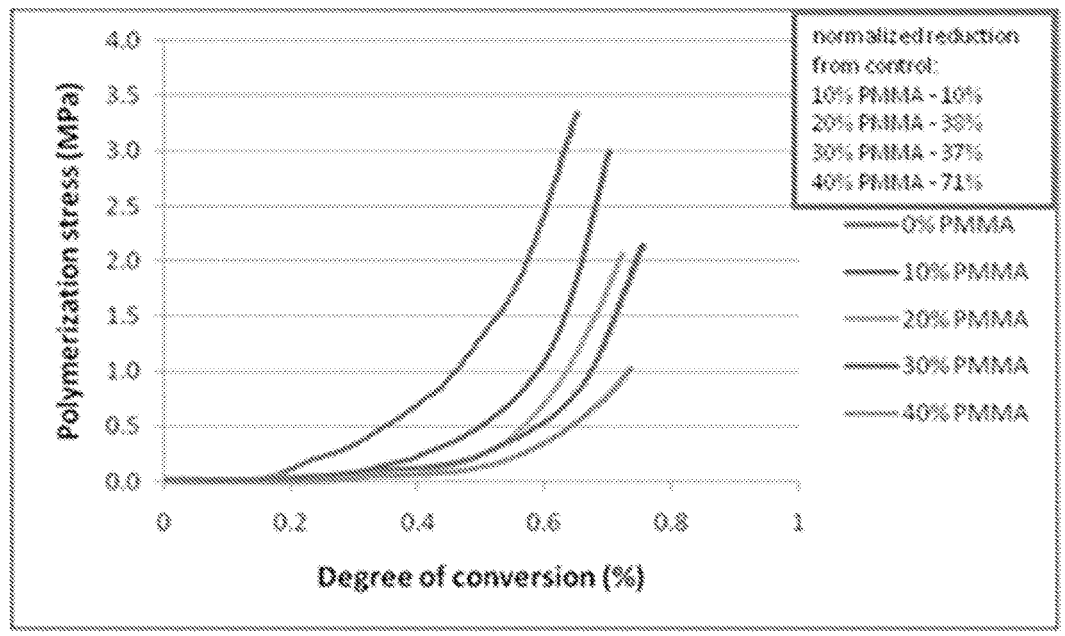
FIG. 10B is a line graph showing the polymerization stress of the indicated compositions as a function of the degree of conversion.
Figure 11A:
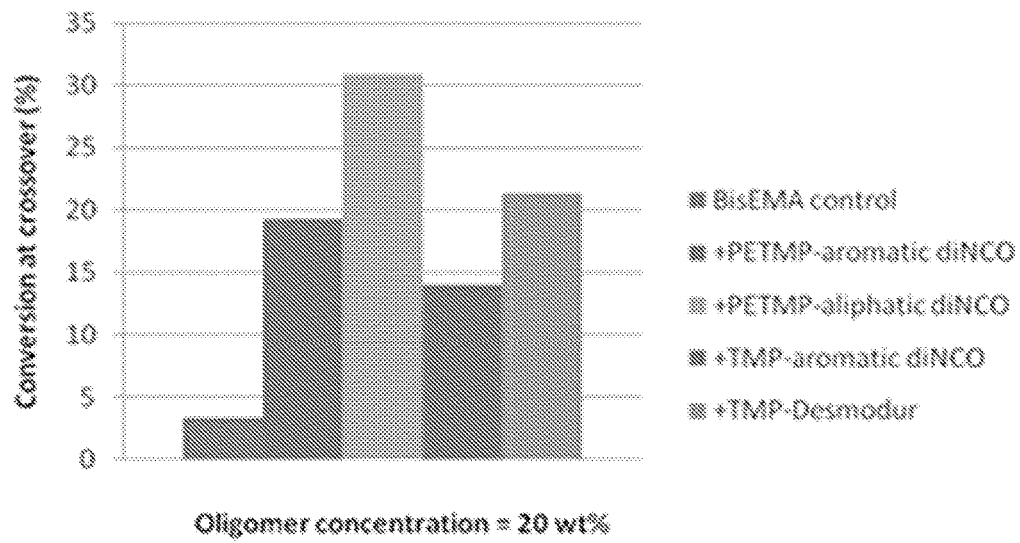
FIG. 11A is a bar graph showing the conversion at crossover for the indicated compositions.
Figure 11B:
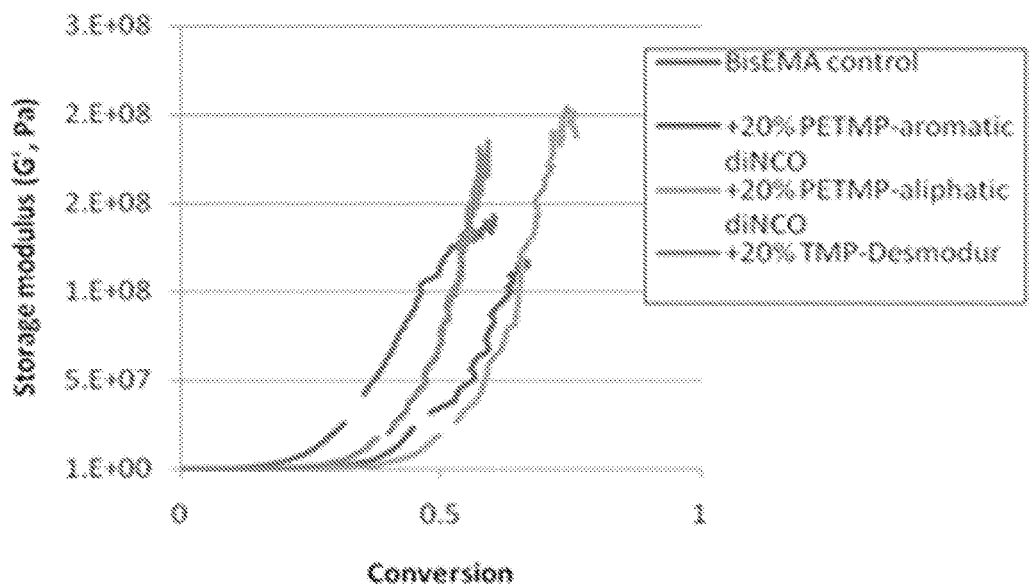
FIG. 11B is a line graph showing the storage modulus of the indicated compositions as a function of the degree of conversion.
Figure 11C:
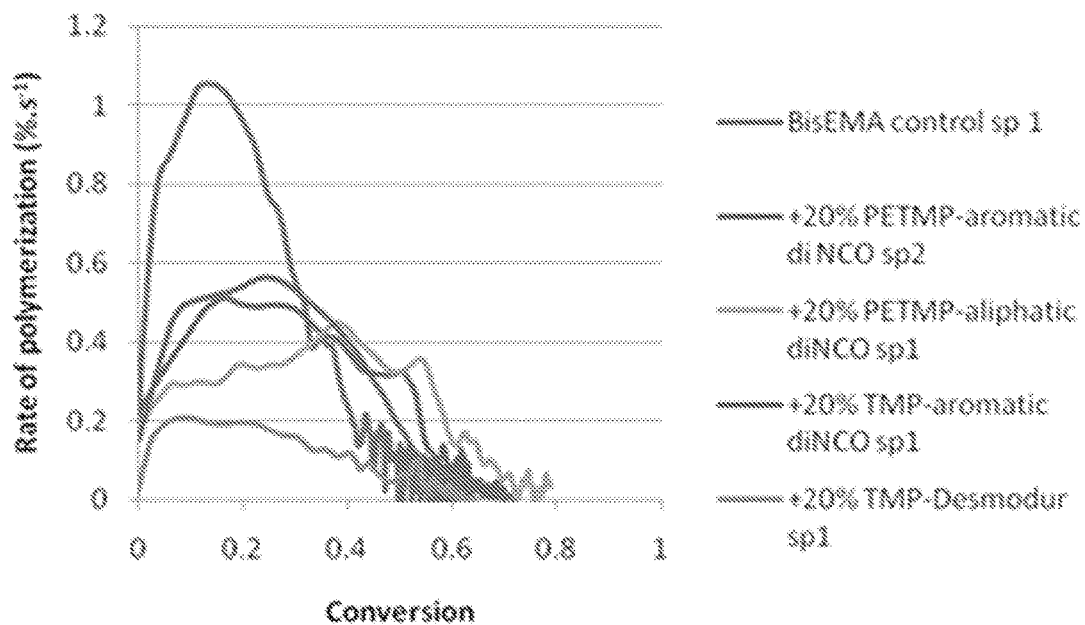
FIG. 11C is a line graph showing the rate of polymerization of the indicated compositions as a function of the degree of conversion.
Figure 12A:
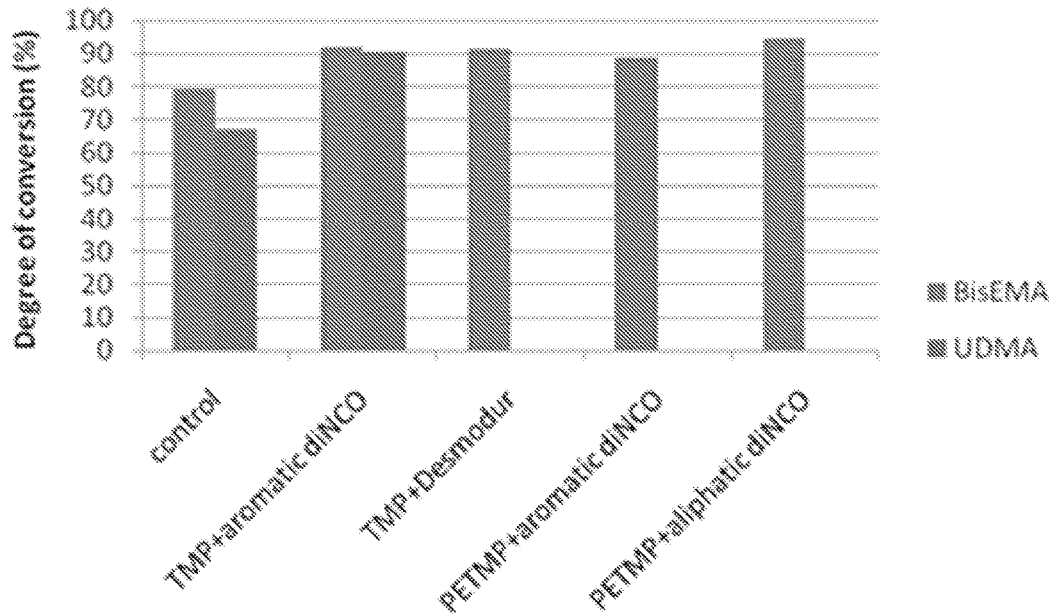
FIG. 12A is a bar graph showing the degree of conversion of the indicated compositions.
Figure 12B:
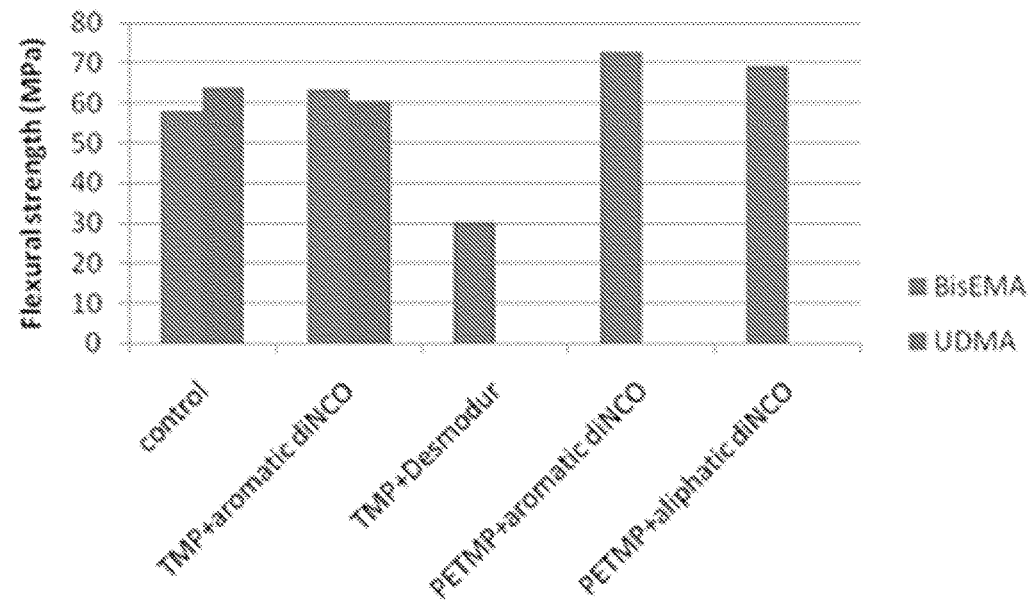
FIG. 12B is a bar graph showing the flexural strength of the indicated compositions.
Figure 12C:
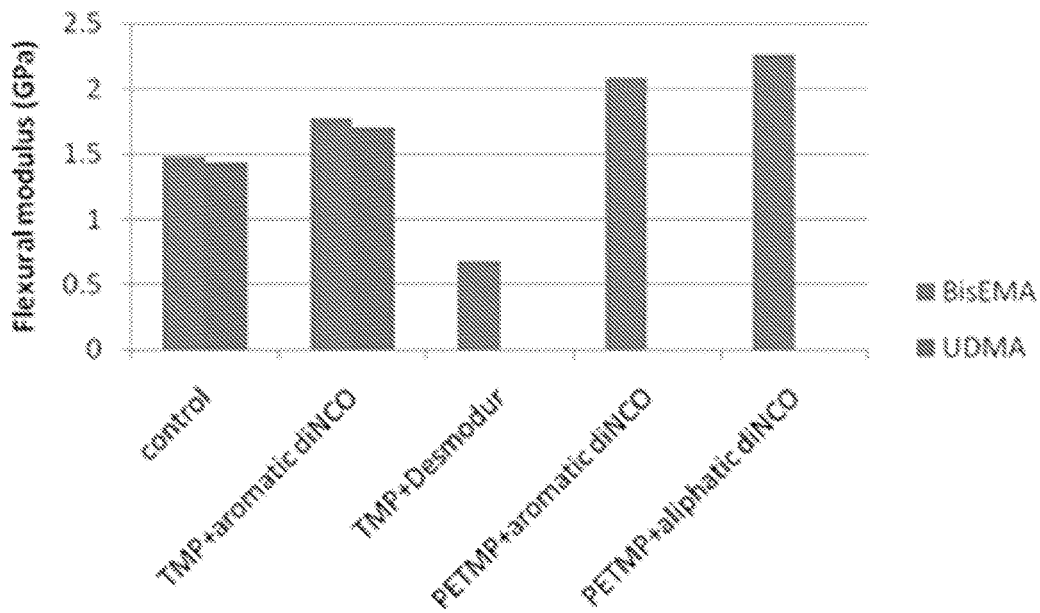
FIG. 12C is a bar graph showing the flexural modulus of the indicated compositions.
Figure 12D:
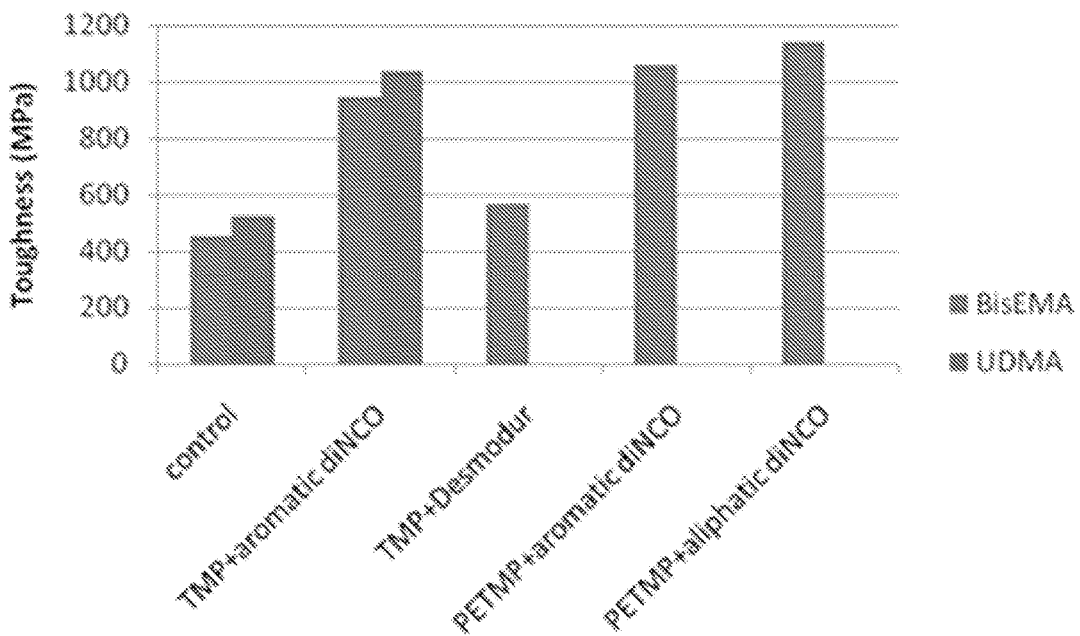
FIG. 12D is a bar graph showing the toughness of the indicated compositions.

Fracture toughness in cements with both aromatic and aliphatic thiourethanes added was statistically higher than the control. The cement with the highest fracture toughness was the cement with 20% aliphatic thiourethane. (p=0.001). Experimental cement with 20% aliphatic thiourethane added also had significantly higher fracture toughness than an identically formulated cement with 20% aromatic thiourethane. (p=0.011). Interaction between the two factors was significant (p=0.034). Cements comprising 10% and 20% aromatic thiourethanes had 88.8% and 108.5% greater fracture toughness (respectively) than controls while cements comprising 10% and 20% aliphatic thiourethanes had 105.9% and 176% greater fracture toughness than controls (FIG. 8A). The proprietary cement with 20% added aromatic thiourethane had a significantly higher fracture toughness (p=0.020) 25.5% greater than that of the control. The proprietary cement with 10% added aromatic thiourethane was similar to the control (FIG. 8B).

Example 8

Thiourethanes Improve the Mechanical Properties of Dual-cured Resin Cements

Dual-cured resin cements are extensively used in Restorative Dentistry. Examples of their clinical applications include the bonding of ceramic fragments, crowns, bridges and intracanal posts. Due to the tapered configuration of the tooth preparation for indirect restorations, characteristics such as resistance to dissolution, strong bond to structures and excellent mechanical properties are requisites for cement materials (Meyer J M et al, *Biomaterials* 19, 529-539 (1998); Rosenstiel S F et al, *J Prosthet Dent* 80, 280-301 (1998); and Manso A P et al, *Dent Clin North Am* 55, 311-332 (2011); all of which are incorporated by reference herein. Currently available methacrylate-based materials present some drawbacks, such as polymerization shrinkage values between 1.77% and 5.28% (Spinel) T et al, *Dent Mater* 25, 1058-1066 (2009); incorporated by reference herein). Polymerization shrinkage increases the risk of stress concentration and gap formation at the interface of cementation. This can ultimately lead to adhesion failure and reduced treatment longevity. Cohesive/adhesive failures at the cement line have been reported (D'Arcangelo C et al, *Oper Dent* 34, 328-336 (2009); incorporated by reference herein).

At least for more heavily filled composites, reduction in polymerization shrinkage and stress can be accomplished with the addition of pre-polymerized particles (Moraes R R et al, *Dent Mater* 27, 509-519 (2011); incorporated by reference herein). The addition of pre-polymerized particles reduce the concentration of saturated methacrylates available to react—in other words, the potential for shrinkage is reduced. In addition, the problem of excess polymerization stress can also be addressed through the addition of thiol-modified materials (for example, thiol-ene oligomers), resulting in delayed vitrification. Thiol-ene oligomers reduce polymerization stress via chain-transfer reactions of the thiol to the ene/vinyl. This results a more homogeneous network formation. Not only does the addition of pre-polymerized particles result in reduced polymerization stress, it also results in an increased degree of conversion (Lu H et al, *Dent Mater* 21, 1129-1136 (2005); Cramer N B et al, *Dent Mater* 26, 21-28 (2010); and Boulden J E et al, *Dent Mater* 27, 267-272 (2011); all of which are incorporated by reference herein). Even though the thiol-ene oligomers display the above advantageous material properties, they also display material instability and somewhat decreased mechanical properties (Lu H et al, 2005 supra).

Thio-urethane oligomers present an attractive alternative to common unfunctionalized pre-polymers and even thiol-ene oligomers because of the high toughness values imparted by the flexible thio-urethane bonds to the polymer matrix, allied with overall more homogeneous network formation (Senyurt A F et al, *Macromolecules* 40, 3174-3182 (2007); incorporated by reference herein). Thiol/isocyanate reactions have been used as two-part systems for applications requiring high fracture toughness and impact resistance (Senyurt et al, 2007 supra).

One approach that has not been attempted for dental applications so far is the use of thiol-terminated thio-urethane oligomers as additives in methacrylate matrices. Pendant thiol functionalities result in delayed gelation. This in turn reduces polymerization stress, increases conversion, and improves network homogeneity—Pfeifer C et al, IADR General Session and Exhibition (2012), the reduction in shrinkage through the addition of pre-polymerized particles (Moraes et al, 2011 supra) and the increase in toughness/fracture toughness through the flexible thio-urethane bonds (Senyurt et al, 2007 supra). Finally, by improving fracture toughness, we expect to improve the bond strength of indirect restorations cemented with the thio-urethane modified cements.

Oligomers were synthesized based on thio-urethane chemistry, containing pendant thiol functionalities for improving the properties of dual-cured resin cements. Thiourethanes were shown to (I) increase the degree of conversion, (II) improve mechanical properties, (III) reduce the polymerization stress of a secondary crosslinked methacrylate network and (IV) improve the bond strength of resin composites and ceramics to dentin.

This example describes the addition of thio-urethane oligomers to dual-cure resin cements. Addition of thio-urethane oligomers especially improves fracture toughness, and reduces polymerization stress. Thiol-functionalized oligomers were synthesized by combining 1,3-bis(1-isocyanato-1-methylethyl)benzene (TMXDI) with trimethylol-tris-3-mercaptopropionate (TMP), at a ratio of 1:2 isocyanate:thiol. The resulting thio-urethane oligomer was added at 0%, 10% or 20% by weight to an experimental cement that included a BisGMA-UDMA-TEGDMA (BUT) mixture at, 5:3:2 and 25% by weight of silanated inorganic fillers.

Alternatively, the thio-urethane oligomer was added to RelyX™Ultimate Adhesive Resin Cement from 3M—a proprietary commercial cement.

Near-IR was used to follow methacrylate conversion after photoactivation (700 mW/cm2×60 s) and after 72 hours. Flexural strength/modulus (FS/FM) and toughness were evaluated in three-point bending with 2×2×25 mm bars. Fracture toughness ($K_{1c}$) was assessed in 2×5×25 mm notched specimens. Polymerization stress was measured on the Bioman. The microtensile bond strength (μTBS) of an indirect composite and a glass ceramic to dentin was also evaluated. Results were analyzed with ANOVA/Tukey's test ($\alpha=5\%$).

In the experimental BUT cements, the addition of thio-urethane oligomers did not affect conversion values. FS/FM increased significantly in both 10% and 20% by weight thio-urethane oligomers, including 3-fold greater toughness in the BUT cement comprising 20% thio-urethane oligomer relative to the control. Cements comprising thio-urethane oligomer had 2-fold greater fracture toughness (p=0.001) than the control. Additionally, the BUT cement comprising thio-urethane oligomers showed 40-50% less stress.

Proprietary cement comprising thio-urethane oligomers had similar conversion rates at 72 h, FS, and toughness compared to the control. Proprietary cement with 20% by weight thio-urethane oligomers had lower FM than the control, potentially due to the dilution of the filler content. Resultantly the proprietary cement comprising thio-urethane oligomers had less stress than the controls. $K_{1c}$ in proprietary cement comprising thio-urethane oligomers was 50% higher than that of controls. Furthermore, the μTBS of an indirect composite comprising 20% by weight thio-urethane oligomer (p=0.039) and of a glass ceramic comprising 20% by weight thio-urethane oligomer (p=0.005) to dentin was higher than that of the control.

Thio-urethanes increase toughness, fracture toughness and bond strength while reducing stress in dual-cured cements, without compromise to the conversion and without alteration to current application techniques.

Methods: Oligomers were synthesized by combining 1,3-bis(1-isocyanato-1-methylethyl)benzene with trimethylol-tris-3-mercaptopropionate in solution, at 1:2 isocyanate:thiol, resulting in pendant thiols from the aromatic (AR) oligomer structure. Thio-urethane oligomers were added to the cements at 0 (control), 10 and 20 wt %.

The experimental dual-cured resin cement was composed of Bis-phenol A diglycidyl dimethacrylate (Bis-GMA), urethane dimethacrylate (UDMA) and tri-ethylene glycol dimethacrylate (TEGDMA), all from Esstech (Essington, Pa., USA) in a 50:30:20 mass ratio (BUT materials). 0.2 wt % of dl-camphoroquinone, 0.6 wt % of a tertiary amine (EDMAB—ethyl 4-dimethylaminobenzoate), and 0.8 wt % inhibitor (BHT—2,6-di-tert-butyl-4-methylphenol; Sigma-Aldrich, St. Louis, Mo., USA) were added to paste A. 0.5 wt % of benzoyl-peroxide was added to paste B (Sigma-Aldrich).

Filler was introduced at 25 wt % (15% OX-50-0.04 mm; 85% silica 0.7 μm, Esstech), with the aid of a mechanical mixer (DAC 150 Speed mixer, Flacktek, Landrum, S.C., USA) operated for 5 min at 2400 rpm. All procedures were carried out under safe yellow light.

One BisGMA/TEGDMA-based commercially available dual-cured cement (RelyX Ultimate®, 3M Espe, St. Paul, USA—lot 498131, translucent) was also used for the study. The material was used as received or modified by the addition of 10 and 20 wt % of oligomer to the organic matrix. According to the information provided by the manufacturer, this resulted in cements with filler contents of 66, 63.6 and 60.8 wt %, respectively.

Materials were mixed immediately before use. Composite discs (0.8 mm thick, 10 mm in diameter, n=3) were formed between two glass slides. Degree of conversion was obtained using near-infrared (NIR) spectroscopy (2 scans/spectrum, 4 cm$^{-1}$ resolution, greater than 2 Hz data acquisition rate) based on the methacrylate vinyl overtone at 6165 cm$^{-1}$ (Stansbury J W & Dickens S H Dent Mater 24, 1-8 (2001); incorporated by reference herein) before and after 60 seconds of direct irradiation with a LED light source (Bluephase, Ivoclar Vivadent, Lichtenstein) at an incident irradiance of 700 mW/cm$^2$.

Bar specimens (n=10, 2×2×25 mm) were fabricated between glass slides and photopolymerized as described above, then stored dry for one week in dark containers at room temperature. Flexural strength of the samples was measured according to ISO 4049 (Standard I, 2000) in 3-point bending using a universal test machine (Q-test, MTS, Eden Prairie, Wis.) at a cross-head speed of 0.5 mm/min. Elastic modulus (GPa) was determined from the slope of the initial linear part of stress-strain curve. Toughness (MPa) was calculated from the integration of the stress×stain curve (Origin 9.1, OriginLab Corporation, Northampton, Mass., USA).

The fracture toughness of all materials was determined from the stress intensity factor (K) during crack propagation. To determine the fracture toughness (FT), single-edge notch beam (SENB) specimens (n=5) were fabricated according to ASTM Standard E399-90 (Designation A, 1997) in a 5×2× 25 mm split steel mold with a razor blade providing a 2.5 mm notch in the center of the specimens. The bending fracture test was performed at a cross-head speed of 0.5 mm min$^{-1}$ using a universal test machine (Q-test) and the fracture toughness (critical stress intensity factor, $K_{IC}$) was calculated as previously described (Ferracane & Berge 1995).

Polymerization stress development was followed in real-time for 30 min using the Bioman, described previously (Watts D C & Satterthwaite J D Dent Mater 24, 1-8 (2008); incorporated by reference herein). Briefly, the resin cement (n=5) was inserted into a 0.5-mm gap corresponding to a C-factor 4, then photoactivated through the glass during 60 s at an incident irradiance of 670 mW/cm$^2$ (Bluephase).

Thirty-six caries-free human third molars extracted for periodontal reasons were used for the microtensile bond strength test. Deep dentin was exposed by cutting the occlusal crown 2.0 mm above the CEJ. The commercial cement (control and modified groups with 10 and 20 wt % of oligomer) was used with an etch-and-rinse adhesive (Adper Singlebond 2; 3M ESPE) for bonding an indirect composite (Z250, 3M ESPE) or a glass ceramic (IPS Empress, Ivoclar Vivadent). Samples (n=6) were stored for one week in distilled water (37° C.) before being sectioned in ~1 mm$^2$ match-sticks for μTBS evaluation in an universal testing machine (0.5 mm/min). Failure pattern was determined by stereomicroscopy/SEM.

Data in all experiments were analyzed by one-way ANOVA and Tukey's test for multiple comparisons ($\alpha=0.05\%$).

Results: Degree of conversion was not affected by the addition of thio-urethanes to the experimental (BUT) cement either when measured immediately after photoactivation (p=0.145) or after 72 h (p=0.053). For the proprietary material, thio-urethane modified groups showed a statistical reduction in DC when evaluated immediately (p=0.002), but where similar to the control after 72 h storage (p=0.930). Results are summarized in Table 4.

TABLE 4

Mean and standard deviation for degree of conversion (%) for experimental and proprietary cements immediate after light irradiation and after 72 h. Values followed by the same superscript within the same test are statistically similar ($\alpha = 5\%$).

Degree of conversion (%)

|  | Experimental | | Proprietary | |
| --- | --- | --- | --- | --- |
|  | immediate | After 72 h | immediate | After 72 h |
| Control | 70.6(2.3)$^a$ | 80.7(2.4)$^a$ | 65.8(0.8)$^a$ | 69.5(1.7)$^a$ |
| 10 wt % | 72.4(1.0)$^a$ | 83.5(1.5)$^a$ | 59.7(3.2)$^b$ | 69.5(1.4)$^a$ |
| 20 wt % | 73.7(1.1)$^a$ | 85.1(0.8)$^a$ | 54(1.7)$^b$ | 69.9(0.9)$^a$ |

Flexural strength and modulus was significantly higher in the thio-urethane-modified BUT materials in relation to the control at both 10% by weight thio-urethane oligomer and 20% thio-urethane oligomer by weight (p=0.001. The toughness was 3-fold higher in the BUT materials with 20% thio-urethane oligomer by weight (p=0.001. The addition of thio-urethanes to the proprietary cement did not significantly affect FS (p=0.345) or toughness (p=0.202). However, thio-urethanes in proprietary cement resulted in a composite with the FM significantly lower than the control (p=0.018) for the 20% by weight thio-urethane oligomer. Results are summarized in Table 5.

TABLE 5

Mean and standard deviations for flexural strength, flexural modulus and toughness for experimental (BUT) and proprietary (PR) cements. Also shown in the table are data of microtensile bond strength (µTBS) of an indirect composite and glass ceramic to dentin for the proprietary (PR) cement modified with thio-urethanes. Values followed by the same superscript within the same test are statistically similar ($\alpha = 5\%$).

|  | Flexural strength (MPa) | | Flexural modulus (GPa) | | Toughness (MPa) | | µTBS composite | µTBS ceramic |
| --- | --- | --- | --- | --- | --- | --- | --- | --- |
|  | BUT | PR | BUT | PR | BUT | PR | PR | PR |
| Control | 94.5 (16.5)$^b$ | 134 (15.3)$^a$ | 2.2 (0.25)$^b$ | 5.5 (0.44)$^a$ | 3.37 (1.48)$^b$ | 1.95 (0.57)$^a$ | 23.1 (4.47)$^b$ | 15.3 (2.89)$^b$ |
| 10% | 119.8 (15.5)$^a$ | 129.1 (20.5)$^a$ | 2.8 (0.16)$^a$ | 4.9 (0.67)$^{ab}$ | 3.89 (1.54)$^b$ | 1.81 (0.49)$^a$ | 26.95 (1.66)$^{ab}$ | 16.7 (3.25)$^{ab}$ |
| 20% | 131.6 (6.6)$^a$ | 121.5 (16.3)$^a$ | 2.8 (0.24)$^a$ | 4.3 (0.11)$^b$ | 10.22 (2.61)$^a$ | 2.36 (0.84)$^a$ | 28.41 (2.05)$^a$ | 21.4 (2.17)$^a$ |

Figure 13A:
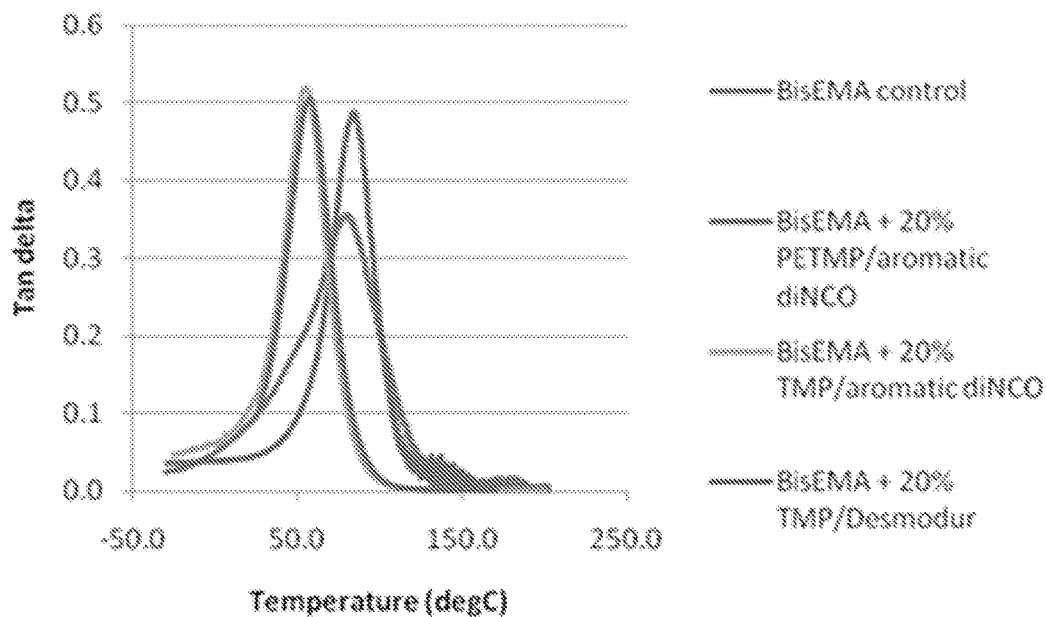
FIG. 13A is a line graph of the tan delta of the indicated compositions as a function of temperature.

Thio-urethane groups resulted in stress values significantly lower than that of the control when added to the experimental cement (p=0.003). A cement comprising 10% and a cement comprising 20% thiourethane oligomer resulted in stress values 40.9% and 53.4%, lower than controls respectively. A statistically significant difference was also observed when a cement comprising 20% thio-urethane was used in the proprietary cement (p=0.001 with a stress value 65.7% lower than the control. Results are summarized in FIG. 13A.

Figure 13B:
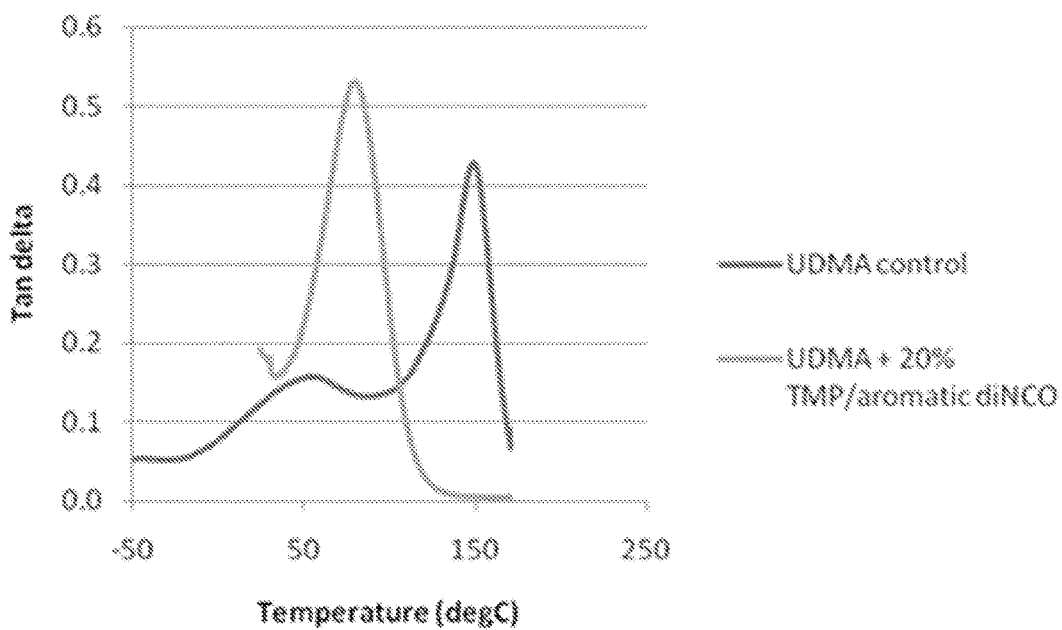
FIG. 13B is a line graph of the tan delta of the indicated compositions as a function of temperature.
Figure 14A:
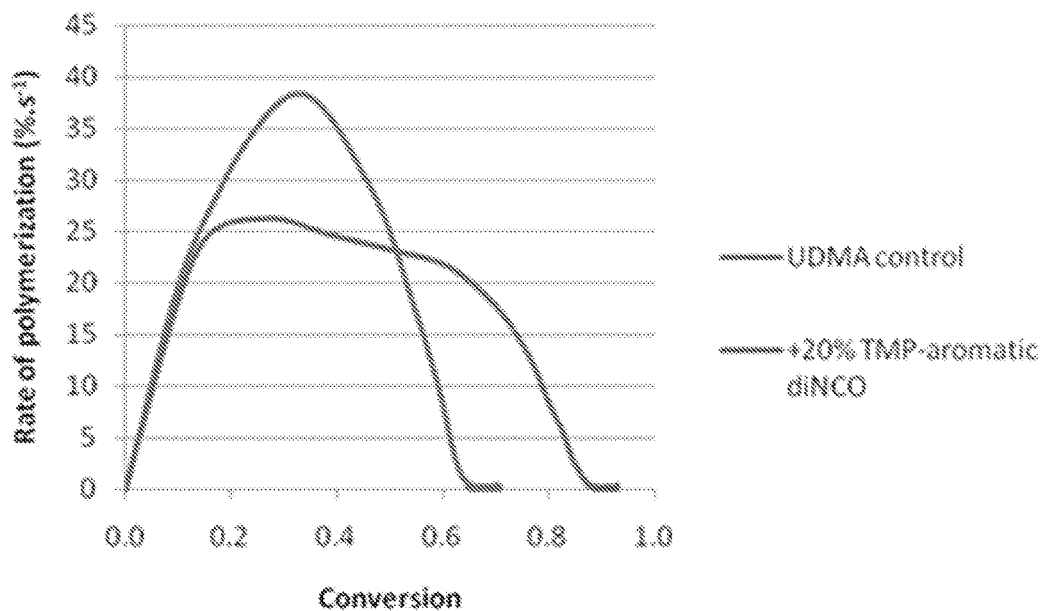
FIG. 14A is a line graph of the rate of polymerization of the indicated compositions as a function of the degree of conversion.
Figure 14B:
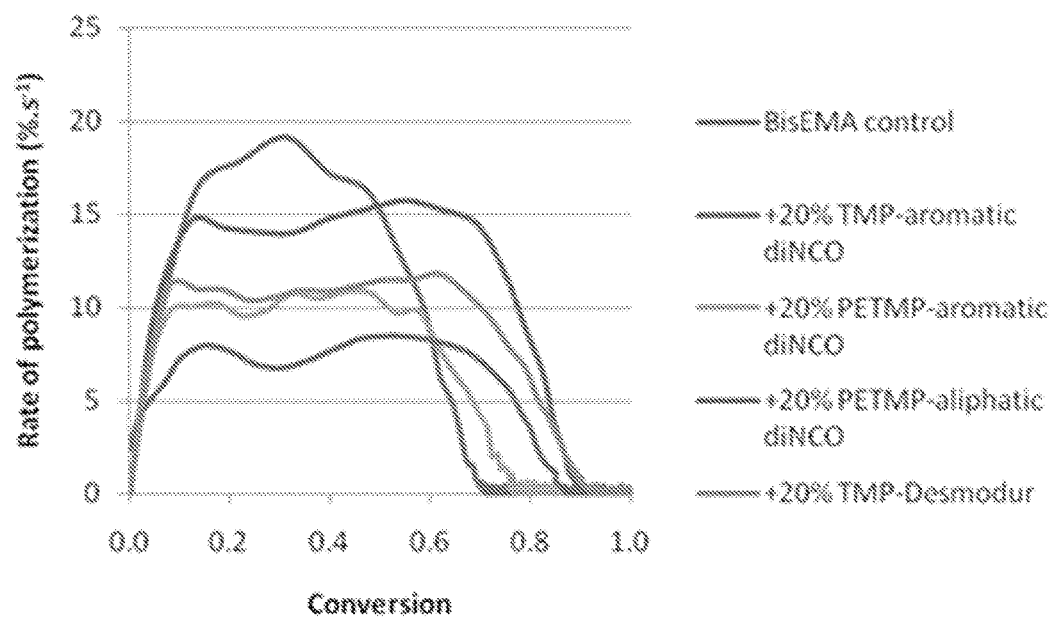
FIG. 14B is a line graph of the rate of polymerization of the indicated compositions as a function of the degree of conversion.

A statistically significant difference in fracture toughness was observed in experimental cements comprising 10% and 20% thiourethane oligomers. (p=0.001. The cement comprising 10% thiourethane oligomers had a 54.5% higher fracture toughness relative to control and the cement comprising 20% thiourethane oligomers had a 136.3% higher fracture toughness relative to the control. A significant difference was observed when 20% thio-urethane oligomer was added to the proprietary cement (p=0.002). The cement with the 20% thio-urethane oligomer had a 50% higher fracture toughness value than the control. Results are summarized in FIG. 13B.

The addition of 20% thio-urethane oligomer resulted in significantly better µTBS values for both indirect composite (p=0.039) and glass ceramic (p=0.005). Results are summarized in Table 5 above. In addition, the failure patterns mixed for all groups with control groups presenting smoother fracture surfaces in comparison to the modified groups.

Example 9

Delayed Gelation and Stress Reduction in Methacrylate Networks Modified by Thio-urethane Oligomers Small molecule thiols have been used in combination with enes and methacrylates to render delayed gelation/vitrification and reduced stress in many polymer applications, including dental restorative materials, coatings, auto-parts, amongst others (Hoyle, C E et al, J Polymer Sci Part A—Polymer Chem 42, 5301-5338 (2004); incorporated by reference herein). Thiol-enes polymerize through a step growth mechanism, in which chain-transfer reactions of the thiol to the double bond postpone network formation and modulus development towards the end of the polymerization reaction, at high conversions (Pfeifer C S et al, Polymer 52, 3295-3303 (2011) and Lu H et a, 2005 supra). This results in decreased stress development and also in more homogeneous networks (Carioscia J A et al, J Polymer Sci Part A—Polymer Chem 45, 5686-5696 (2007); incorporated by reference herein). However, some drawbacks of these thiol-modified networks still remain, especially in terms of mechanical properties (Boulden J E et al, 2011 supra).

By judiciously selecting the structure of the thiol and ene or by combining thiol-enes in ternary systems with methacrylates, it is possible to partially circumvent the decreased toughness and fracture toughness typical of networks formed with flexible thioether bonds. As for the foul odor commonly associated with small, volatile thiol molecules, the choice or design of higher weight thiols is known to alleviate this problem. Another potential disadvantage is the stability of thiol-modified vinyl compounds in the presence of bases, such as the amines that comprise part of the initiator system in dental composites (Esfandiari P et al, J Polymer Sci Part A: Polymer Chem 51, 4261-4266 (2013); incorporated by reference herein). The presence of bases can initiate a Michael addition reaction and severely decrease shelf-life of these materials, especially if exposed to higher temperatures (Chan J W et al, Eur Polymer J 45, 2717-2725 (2009); incorporated by reference herein).

One approach that may help overcome some of these drawbacks is the use of pre-polymerized networks containing thiols. The synthesis of oligomers designed to leave pendant thiols from the backbone structure is known in the art. These oligomers are made tougher by the choice of stiffer ene structure. The use of polyurethanes as additives in methacrylate networks has been proposed in the art. This has gained broad acceptance due to improved surface quality and reduction of delamination and warping in, for example, molded parts (Li W et al, Polymer 41, 697-710 (2000); incorporated by reference herein). Recent studies have investigated the performance of thio-carbamate (or thio-urethane) networks as compared to simple urethane counterparts (Li Q et al, Macromolecules 42, 1824-1833 (2009); incorporated by reference herein). These materials represent an alternative to pure thiol-ene or pure urethane networks. Indeed, it has been shown that thio-urethanes present more homogeneous networks compared to urethanes (as demonstrated by dynamic mechanical analysis studies, with narrower tan delta peaks), increased conversion and greater toughness and optical clarity (high refractive index). All those features make them attractive for use as additives in dental materials.

Thio-urethanes are obtained through the reaction between thiols and isocyanates in the presence of a base, and can be polymerized in solution to yield oligomers with controllable properties and pendant thiols (Shin J et al, Macromolecules 42, 3294-3301 (2009); incorporated by reference herein). In this specific case, the advantages of synthesizing an oligomer instead of having the thiol-isocyanate reaction take place in situ are as follows: 1. Oligomers can be used as additives into secondary networks (for example, methacrylates), which would avoid the need for two-part formulations or the more complicated free radical and photo-base systems; 2. Oligomers also decrease the concentration of polymerizable functionalities, which leads to volumetric shrinkage reduction; 3. Polymerizations in solution with further purification ensures the complete consumption of isocyanates during the synthesis of thio-urethanes, so that biological concerns are minimized; 4. By using appropriate ratios of thiol to isocyanate, oligomers with pendant thiol functionalities can be designed to perform further chain-transfer reactions with a secondary monomer matrix.

Based on the potential for reduction of polymerization shrinkage and stress and for the improvement of conversion and general mechanical properties, this Example describes the synthesis of several examples of thio-urethane networks, with varying crosslinking ratios and glass transition temperatures, and to further incorporate the pre-polymerized networks into a secondary methacrylate matrix. Covalent bonding between the oligomers containing pendant thiols and the monomer is given by thiol-methacrylate reactions involving chain-transfer, which is expected to help delay gelation and contribute a more homogeneous network.

Materials: Thiourethane oligomer synthesis: Thio-urethane oligomers were synthesized by combining isocyanates (1,6-hexanediol diisocyante (HDDI—aliphatic isocyanate), 1,3-bis(1-isocyanato-1-methylethyl)benzene (BIMB—aromatic isocyanate) or bis(4-isocyanotocyclohexyl) methane (HMDI, cyclic isocyanate) with thiols of increasing functionality (methyl-3-mercaptopropionate (MMP), trimethylol tris-3-mercaptopropionate (TMP) or pentaerythritol tetra-3-mercaptopropionate (PETMP)). A 1:2 ratio of isocyanate to thiol functional groups was used to prevent gelation (according to the Flory-Stockmeyer gelation theory) and leave reactive thiol groups appended to the oligomer structure. Reagents were added to a four-fold excess of methylene chloride in a round-bottom flask, stirred under nitrogen purge for 20 min at room temperature before a catalytic amount of triethylamine (TEA) was added. The reaction was then allowed to proceed for 6 h under nitrogen purge. The resulting oligomers were purified by precipitation in hexanes and good yields were obtained after solvent removal under reduced pressure. Materials were characterized by mid-IR (Nexus 6700, Thermo-Nicolet, Madison, Wis., USA), 1H-NMR (500 Hz, Varian, Palo Alto, Calif., USA) and gel permeation chromatography (triple detection GPC, Viscotek, Houston, Tex., USA).

Experimental material formulation and irradiation conditions: The oligomers were added to ethoxylated bisphenol A dimethacrylate (BisEMA, Esstech, Essington, Mass., USA) or urethane dimethacrylate (UDMA, Esstech) at 20 wt %. 2,2-Dimethoxy-2-phenylacetophenone (DMPA, $\lambda_{max}$=365 nm) was added at 0.1 wt % as the UV initiator and 3,5-di-t-butyl-4-hydroxytoluene (BHT) was added at 0.2 wt % as a radical polymerization inhibitor. Materials were polymerized with a mercury arc lamp filtered to 320-390 nm, at 30 mW/cm$^2$ (unless otherwise noted).

Polymerization stress coupled with conversion: Polymerization stress development was followed in real-time with methacrylate conversion using the American Dental Association—Health Foundation tensometer, as previously described (Lu H et al, J Mater Sci Mater in Med 15, 1097-1103 (2004); incorporated by reference herein). Briefly, the material is placed between two glass rods, attached to the fixed base of the apparatus and to a deformable cantilever beam. As the material polymerizes and shrinks, it causes a deflection in the beam and the stress is then calculated based on the cross-sectional area of the specimen and a calibration curve of the beam constant obtained previously. Rate of stress development (Rs) was calculated as the first derivative of the stress versus time curve. Fiber optic cables provide remote monitoring of vinyl conversion through real-time near-IR spectroscopy.

Rheometry coupled with conversion and dynamic mechanical analysis: Samples of selected formulations were sandwiched between two 20 mm parallel quartz disc plates, attached to a rheometer and tested in shear at a frequency of 100 rad/s with 5% strain (ensuring that the test was carried out within the linear viscoelastic regime), while being photopolymerized at 0.3 mW/cm$^2$ under nitrogen purge. An optical apparatus developed in our laboratory allowed both UV and near-IR direct transmission access to specimens within the photorheometer so that methacrylate conversion (from the methacrylate first overtone absorption band at 6165 cm$^{-1}$) was remotely followed concomitantly with modulus development. The crossover between G' (storage modulus) and G" (loss modulus) was used as an estimate of the gel point conversion (Chambon F and Winter H H, J Rheology 31, 683-697 (1987); incorporated by reference herein. Maximum rate of polymerization ($Rp_{max}$) was obtained from the first derivative of the degree of conversion (DC) versus time kinetic curves. Plots of $Rp_{max}$ normalized by the vinyl concentration ($Rp_{max}$/[M]) were also constructed. Bar-shaped specimens (1×3×25 mm) were polymerized to their limiting conversion (10 min at 1200 mW/cm$^2$ filtered to 320-390 nm; with post-cure thermal treatment at 180° C. for 6 h) and then tested in tension in a dynamic mechanical analyzer (Q80, TA Instruments) during a temperature scan from 200 to −50° C. (3° C./min).

Bulk mechanical properties: Flexural strength and modulus were evaluated on 2×2×25 mm bars in three-point bending, with 20 mm span between the supports, tested at a cross-head speed of 1 mm/min (according to ASTM D-790). Dynamic mechanical analysis of polymerized specimens (photoactivation followed by thermal treatment at 120° C. for 6 h to ensure conversions higher than 90%) was carried out in a Q80 DMA (TA Instruments) on 1×3×15 mm bars in tension mode, with 0.01% strain, at a rate of 3° C./min, from 200 to −30° C. Glass transition temperatures of isolated bulk oligomers were determined with 10 mg of material sandwiched in a thin metallic pocket on a DMA 8000 (Perkin Elmer, Waltham, Mass., USA), with 0.05% strain, at a rate of 3° C./min, from 200 to −30° C.

Statistical analysis: Two-way analysis of variance/Tukey's test was used as the statistical method, once the results have shown normal distribution and homocedasticity. A sample size of three for the tensometer, rheometer and DMA experiments and five for the flexural tests has been shown to provide sufficient power to the statistical analysis, at a 95% confidence level.

Results: In general, the addition of the branched oligomers to either of the methacrylates tested in this study increased final conversion and decreased $Rp_{max}$ in relation to the unmodified controls. At least for BisEMA, a monomer with relatively low viscosity, the pre-polymerized particles impose mobility restrictions earlier in conversion compared to the control: termination becomes diffusion controlled sooner, favoring propagation at slower rates, which delays the end of autoacceleration to higher conversions. That is reflected by early rates values (at 10% conversion), which are lower for the modified groups compared to the control (Table 6), as well as by the higher conversion values at $Rp_{max}$ (Table 6).

development of diffusional limitations to propagation. Results have shown this to be dependent on the oligomer backbone structure.

Within groups of oligomers made with the same thiol (PETMP or TMP), $Rp_{max}$ decrease and final conversion increase were less pronounced for the more hindered, aromatic isocyanate. When comparing oligomers made with the same diisocyanate (aromatic version), the tri-functional thiol (TMP) was less efficient in reducing $Rp_{max}$ than the tetra-functional thiol (PETMP), but reached higher conversion. This is probably due to the fact that one less thiol-terminated flexible arm is available on the backbone of TMP, which may slightly increase stiffness, but probably more importantly, will result in less unreacted thiol functionalities compared to PETMP (i.e., the effective thiol concentration is lower). In multifunctional molecules, the reactivity of functional groups significantly decreases once one end gets incorporated in the polymer network, which may explain the lower reactivity and earlier vitrification (hence lower limiting conversion) of PETMP/aromatic diisocyanate compared to the TMP counterpart. The most flexible structure (PETMP combined with the aliphatic diisocyanate) was the most efficient in decreasing rate of polymerization, but because of the limiting reactivity of the thiol functionalities past a certain point in conversion, was not able to delay vitrification (increase conversion at vitrification) and increase final conversion as significantly as any of the TMP-based oligomers. Despite differences between oligomer species, conversion at deceleration was approximately 40% lower for the control, meaning that all oligomers were efficient in delaying vitrification. This led to increases in final conversion of 10-20%, both for BisEMA and for UDMA. The fact that PETMP-aromatic diisocyanate oligomer-containing groups showed slightly lower conversion at vitrification, and

TABLE 6

Kinetic parameters (obtained with the IR data from tensometer), Mc (for crosslinking; obtained with dynamic mechanical analysis) and conversion at crossover for BisEMA- and UDMA-based materials modified with thiourethane oligomers.

| Secondary matrix | Thiourethane | DC (%) | $Rp_{max}$ (% · s$^{-1}$) | Rp at 10% DC (% · s$^{-1}$) | DC at $Rp_{max}$ (%) | Mc | DC at crossover (%) |
|---|---|---|---|---|---|---|---|
| BisEMA | Control | 78.0 ± 1.0 | 19.1 ± 2.5 | 15.4 ± 1.8 | 36.0 ± 3.0 | 0.0017 | 3.4 ± 0.1 |
| | PETMP-aromatic | 86.0 ± 1.0 | 12.0 ± 1.7 | 10.0 ± 2.3 | 49.0 ± 3.0 | 0.0022 | 16.4 ± 3.4 |
| | PETMP-aliphatic | 92.0 ± 1.0 | 9.2 ± 0.8 | 7.2 ± 0.9 | 52.0 ± 7.0 | x | 30.8 ± 2.4 |
| | TMP-aromatic | 96.0 ± 3.0 | 15.9 ± 1.0 | 14.6 ± 1.0 | 57.0 ± 3.0 | 0.0022 | 14.0 ± 4.2 |
| | TMP-cyclic | 99.8 ± 1.0 | 11.9 ± 0.3 | 11.0 ± 0.7 | 60.0 ± 4.0 | 0.0013 | 21.4 ± 1.1 |
| UDMA | Control | 71.0 ± 1.0 | 41.8 ± 3.7 | 30.3 ± 2.6 | 37.0 ± 2.0 | 0.0043 | x |
| | TMP-aromatic | 93.0 ± 1.0 | 26.3 ± 0.7 | 23.5 ± 1.6 | 27.0 ± 2.0 | 0.0024 | x |

In the case of UDMA, an already higher viscosity monomer owing to moderately strong hydrogen bonding interactions, conversion at $Rp_{max}$ actually decreased in relation to the control (due to a possible disruption of some of the secondary molecular interactions), but increased final conversion and decreased $Rp_{max}$ were still observed with the addition of oligomers, meaning that factors other than the simple increase in viscosity influenced kinetics behavior. For pure methacrylates, deceleration almost immediately follows $Rp_{max}$ (end of autoacceleration), while the modified groups show nearly constant rates of polymerizations through a much wider interval in conversion (approximately 10-70% conversion) before deceleration is observed, a clear demonstration of delayed vitrification. This is due to chain-transfer reactions of the pendant thiols to the methacrylate which delay network formation. This in turn delays the slightly lower final conversion compared to the other oligomer-modified materials, can also be explained in terms of its higher Tg, as will be explored further.

While the polymerization kinetics give insight into the vitrification stage, rheology experiments were used to estimate conversion at gelation, via the crossover between storage and loss modulus (G'/G") as they develop with polymerization. It is important to note that the crossover of G'/G" is being used to rank the gelation character of different materials, without necessarily providing absolute gel point conversion data, as this only truly applies for a very limited set of polymers. Even though these experiments were conducted at much lower light intensity and under nitrogen purge (eliminating the effects of oxygen on radical polymerization and thiol-derived chain-transfer), results are in good agreement with the kinetic runs obtained from the tensometer in terms of material's ranking. The crossover between loss and storage modulus, used here as an indication of gel point, was observed for BisEMA at 3.5% conversion, while that value increased in the range of 14-31% for oligomer-modified materials. Also, the point in conversion where modulus significantly rises increased from 10% (control) to 25-35%. These results demonstrate the dependency of delayed gelation potential on the oligomeric structure, and that follows the same rationale already explored in the previous discussion of kinetics.

In general, flexural strength and modulus increased by 7 to 24% and 20 to 53%, respectively, with the addition of oligomers for both monomers (BisEMA and UDMA), which is in part due to the increased conversion observed, but also due to the introduction of thio-urethane bonds. The more homogeneous final network structure and the increased reinforcement associated with the thio-urethane hydrogen bonding promotes toughness that increases both the modulus and ultimate strength. The only exception was the material modified by TMP combined with HMDI (cyclic isocyanate), clearly showing that the combination of a relatively flexible isocyanate with a thiol of lesser functionality dramatically affects mechanical properties, in spite of the higher conversion. This is also evidenced by the toughness values (calculated from the integrated area of the stress×strain plots generated in the flexural test), which for both monomers show a significant increase with the addition of oligomers, ranging from 98 to 134%. However, the TMP-HMDI group showed an increase in toughness in relation to the control of only 17% (note that toughness is still higher than the control, in spite of the much lower flexural strength and modulus—reduced by about 50%). When oligomers produced with the same aromatic isocyanate are compared, the effect of thiol functionality on all mechanical properties is highlighted: the tetra-functional thiol (PETMP) was better able to improve mechanical properties in comparison with its tri-functional counterpart. Higher thiol functionality species produce oligomer networks with a higher concentration of thio-urethane crosslinks in the oligomer network, as well as have more potential for crosslinking through chain transfer with the secondary methacrylate matrix. Toughness and generally better mechanical properties, then, stem from the higher conversion, as already mentioned, a more homogeneous network formed in the presence of chain-transfer reactions by the thiols (as will be discussed in detail in the DMA section), and the great effect of thio-urethane bonds that contribute hydrogen bonding and improved toughness. This effect was more pronounced in BisEMA, which does not present appreciable hydrogen bonding potential to begin with, while for UDMA the presence of the oligomer might actually have decreased the hydrogen bonding potential already present, which explains why the increase in flexural strength and modulus provided by the addition of the oligomer was not as marked for this monomer.

Dynamic mechanical analysis shows that, in general, glass transition temperature decreases with the addition of oligomers (with one exception), due to the introduction of flexible thio-urethane bonds, and that, along with the higher conversion values, helps explain the higher toughness obtained with these materials. The one exception was the material modified by the PETMP/aromatic diisocyanate oligomer, which resulted in a network with Tg similar to that of the original network. This is further evidence for the fact that greater thiol functionality enhances the reinforcing potential of thio-urethane oligomers, since the overall network crosslinking density of the network was similar for TMP and PETMP aromatic isocyanates, both higher than the control (Table X). In the UDMA networks, in spite of the increase in conversion provided by the addition of oligomers, the decrease in Tg was accompanied by a decrease in overall crosslinking density, at least for the lower functionality thiol (TMP) combined with the aromatic isocyanate (the only one tested for UDMA). As expected from the delayed gelation given by the chain-transfer reactions of thiol to methacrylate described for the rheometer experiments, oligomer-modified materials results in more homogeneous networks, as demonstrated by much narrower tan delta peaks in relation to the controls. For BisEMA groups, the breadth of tan delta decreased by approximately 25° C. with the addition of oligomers (36% reduction), while for UDMA the reduction was 60° C., 42% narrower than the control, which is another demonstration of the effects of thio-urethane oligomers in decreasing hydrogen bonding induced microheterogeneity.

As expected from the delayed gelation and vitrification demonstrated with the rheometer experiments, polymerization stress was significantly reduced (24-58% reductions), even with increased conversion and modulus values registered for the modified materials. The onset of stress development was also delayed, which resulted in overall lower final stress at 10-30% higher conversions with the addition of oligomers. As for the small differences among the various types of oligomers, in general, those derived from aromatic diisocyanates resulted in earlier gelation than the aliphatic/cyclic counterparts, as already discussed, which explains not only the earlier onset of stress but also the lowest conversion for the same or slightly higher final stress values. For the same aromatic diisocyanate, the tri-functional thiol (TMP) presented slightly earlier gelation but much later vitrification than the tetra-functional thiol (PETMP), as already discussed, which increased conversion by 5% in the TMP material. That way, in spite of the lower mechanical properties in relation to PETMP, TMP presented higher stress. BisEMA modified by PETMP/aliphatic diisocyanate presented one of the lowest stress values (58% reduction in relation to the control) at almost 95% conversion (25% higher than the control), due to the greatest delay in gelation/vitrification amongst all oligomers. Compared to its aromatic counterpart, the reduction in stress can be explained by the higher conversion at deceleration (greater delay in vitrification), the lower Tg, and slightly lower flexural strength, modulus and toughness (still all higher than the control, however).

In summary, these results have demonstrated significant improvements to a methacrylated network achieved with the use of thio-urethanes as additives. Such additives are produced with a one pot, simple synthesis procedure, taking advantage of the efficient 'click' reaction between thiols and isocyanates, which also provides an effective means to completely eliminate any potential thiol odor in the resin formulation. From the dental restorative material standpoint, higher conversion and over a two-fold increase in toughness were observed in the oligomer-modified materials, while polymerization stress decreased by up to 60%. The use of such additives was accomplished in photopolymerizable networks, with no need to change the restorative procedure.

The invention claimed is:

1. A compound of the formula:

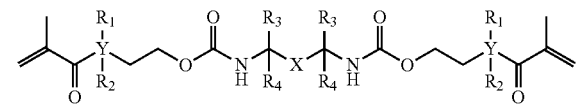

wherein X is aryl or 1-4 carbon alkyl;
Y is N or C;
$R_1$ is H or alkyl and $R_2$ is no atom when Y is N;
$R_1$ is H or alkyl and $R_2$ is H or alkyl when Y is C; and
$R_3$ and $R_4$ are H or alkyl; and
provided that $R_1$ and $R_2$ are not H when X is butyl.

2. The compound of claim 1 wherein X is benzyl.

3. The compound of claim 2 wherein $R_3$ and $R_4$ are each methyl.

4. The compound of claim 3 wherein Y is N and R1 is selected from the group of H, methyl, and ethyl.

5. The compound of claim 3 wherein Y is C and $R_1$ and $R_2$ are each methyl.

6. The compound of claim 1 wherein X is butyl.

7. The compound of claim 6 wherein Y is N and $R_1$ is selected from methyl and ethyl.

8. The compound of claim 6 wherein Y is C and $R_1$ and $R_2$ are both methyl.

9. A dental composite composition comprising:
a resin composition comprising the compound of claim 1;
a thiourethane oligomer; and
a filler composition.

10. The dental composite of claim 9 wherein the thiourethane oligomer is thiol terminated.

11. The dental composite of claim 9 wherein the thiourethane oligomer is isocyanate terminated.

12. A method of preparing a dental composite, the method comprising:
contacting an isocyanate compound selected from 1,6 hexanediol-diisocyanate, 1,3-bis(1-isocyanato-1methylethylbenzen e), or bis(4-isocyanotocyclohexyl) methane with a thiol compound selected from methyl-3-mercaptopropionate, pentaerythritol tetra-3-mercaptopriopionate, and trimethylol-tris-3-mercaptopriopionate in the presence of trimethylamine to make a thiourethane oligomer, wherein the isocyanate compound is added in sufficient excess that the thiourethane oligomer comprises pendant thiols; and
combining the thiourethane oligomer with a tertiary amine, d-camphorquinone, an inhibitor, a filler composition, and a compound of the formula:

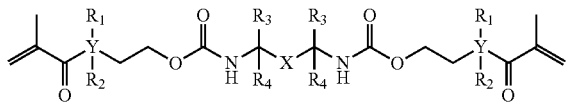

wherein X is aryl or 1-4 carbon alkyl;
Y is N or C;
$R_1$ is H or alkyl and $R_2$ is no atom when Y is N;
$R_1$ is H or alkyl and $R_2$ is H or alkyl when Y is C; and
$R_3$ and $R_4$ are H or alkyl;
provided that $R_1$ and $R_2$ are not H when X is butyl; to form the dental composite;
wherein the thiourethane oligomer comprises at least 10% of the composite.

13. The method of claim 12 wherein the isocyanate compound is added to the thiol compound in a 2:1 ratio.

14. The method of claim 12 wherein the composite comprises at least 0.6% by weight dimethylaminobenzoate.

15. The method of claim 12 wherein the composite comprises at least 0.5% by weight 2,6-di-tert-butyl-4-methylphenol.

16. The method of claim 12 wherein the composite comprises at least 0.2% by weight d-camphorquinone.

17. The method of claim 12 wherein the composite comprises one or more of barium glass, zirconia, or silica.

18. The method of claim 12 wherein the composite comprises at least 25% filler.

19. The method of claim 12 further comprising adding benzoyl peroxide to the composite.

* * * * *

UNITED STATES PATENT AND TRADEMARK OFFICE
CERTIFICATE OF CORRECTION

PATENT NO. : 10,071,027 B2
APPLICATION NO. : 15/126751
DATED : September 11, 2018
INVENTOR(S) : Carmem S Pfeiffer and Jack L. Ferracane It is certified that error appears in the above-identified patent and that said Letters Patent is hereby corrected as shown below:

In the Specification

Please delete the paragraph under the heading ACKNOWLEDGEMENT OF GOVERNMENT SUPPORT from Column 1, Lines 16-21 that appears as:
"The work that resulted in this invention was funded in part by the United States Government under the terms of Grant Number 1R15 DE023211 01A1 and Grant Number 1U01 DE02756 01 awarded by the National Institutes of Health. The United States Government has certain rights to this invention."

And replace it with the passage below:
-- This invention was made with government support under DE023211 and DE023756 awarded by the National Institutes of Health. The government has certain rights in the invention. --

Signed and Sealed this
Sixteenth Day of July, 2019

Andrei Iancu
*Director of the United States Patent and Trademark Office*